(12) United States Patent
Ishikawa et al.

(10) Patent No.: US 8,993,543 B2
(45) Date of Patent: Mar. 31, 2015

(54) DIPHENYL SULFIDE DERIVATIVE AND PHARMACEUTICAL PRODUCT WHICH CONTAINS SAME AS ACTIVE INGREDIENT

(75) Inventors: Kumi Ishikawa, Tochigi (JP); Shigeru Koga, Tochigi (JP); Yasushi Kohno, Tochigi (JP); Kiyoshi Fujii, Tochigi (JP); Ken Yoshikawa, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/883,847
(22) PCT Filed: Dec. 20, 2011
(86) PCT No.: PCT/JP2011/007111
§ 371 (c)(1),
(2), (4) Date: Jun. 12, 2013
(87) PCT Pub. No.: WO2012/086184
PCT Pub. Date: Jun. 28, 2012

(65) Prior Publication Data
US 2013/0261089 A1     Oct. 3, 2013

(30) Foreign Application Priority Data
Dec. 21, 2010  (JP) ................................ 2010-284150

(51) Int. Cl.
*C07F 9/38*   (2006.01)
*C07F 9/09*   (2006.01)
*C07F 9/40*   (2006.01)

(52) U.S. Cl.
CPC . *C07F 9/38* (2013.01); *C07F 9/091* (2013.01); *C07F 9/3808* (2013.01); *C07F 9/4006* (2013.01); *C07F 9/4015* (2013.01)
USPC ........................................................ 514/114

(58) Field of Classification Search
None
See application file for complete search history.

(56) References Cited

U.S. PATENT DOCUMENTS 8,569,270 B2 * 10/2013 Kohno et al. ................. 514/114
2012/0101068 A1    4/2012 Kohno et al.

FOREIGN PATENT DOCUMENTS

| EP | 1 602 660    | 12/2005 |
|----|--------------|---------|
| JP | 2005-247691  | 9/2005  |
| JP | 2010-13407   | 1/2010  |
| JP | 2010-77053   | 4/2010  |
| JP | 2011-32226   | 2/2011  |
| WO | 03/020313    | 3/2003  |
| WO | 2004/074297  | 9/2004  |
| WO | 2006/063033  | 6/2006  |
| WO | 2007/043568  | 4/2007  |
| WO | 2008/018427  | 2/2008  |
| WO | 2008/019090  | 2/2008  |
| WO | 2011/004604  | 1/2011  |
| WO | 2011/138393  | 11/2011 |
| WO | 2011/138398  | 11/2011 |

OTHER PUBLICATIONS

Supplementary European Search Report issued Mar. 5, 2013 in corresponding European Application No. 10796915.6.

International Preliminary Report on Patentability issued Jun. 25, 2013 and English translation of the Written Opinion of the International Searching Authority issued Feb. 28, 2012 for International Application No. PCT/JP2011/007111.
Takuwa et al., "Subtype-specific, differential activities of the EDG family receptors for sphingosine-1-phosphate, a novel lysophospholipid mediator", Molecular and Cellular Endocrinology, vol. 177, 2001, pp. 3-11.
Igarashi, Y., "Sphingosine-1-Phosphate as an Intercellular Signaling Molecule", Annals New York Academy of Sciences, vol. 845, No. 19, 1998, pp. 19-31.
Okazaki et al., "Molecular Cloning of a Novel Putative G Protein-Coupled Receptor Expressed in the Cardiovascular System", Biochemical and Biophysical Research Communications, vol. 190, No. 3, Feb. 15, 1993, pp. 1104-1109.
Gon et al., "S1P$_3$ receptor-induced reorganization of epithelial tight junctions compromises lung barrier integrity and is potentiated by TNF", PNAS, vol. 102, No. 26, Jun. 28, 2005, pp. 9270-9275.
Niessen et al., "Dendritic cell PAR1-S1P3 signalling couples coagulation and inflammation", Nature Letters, vol. 452, Apr. 3, 2008, pp. 654-658.
Keller et al., "Immunomodulator FTY720 Induces Myofibroblast Differentiation via the Lysophospholipid Receptor S1P$_3$ and Smad3 Signaling", The American Journal of Pathology, vol. 170, No. 1, Jan. 2007, pp. 281-292.
Niessen et al., "Endogenous EPCR/aPC-PAR1 signaling prevents inflammation-induced vascular leakage and lethality", Blood, vol. 113, No. 12, Mar. 19, 2009, pp. 2859-2866.
Sanna et al., "Enhancement of capillary leakage and restoration of lymphocyte egress by a chiral S1P$_1$ antagonist in vivo", Nature Chemical Biology, vol. 2, No. 8, Aug. 2006, pp. 434-441.
International Search Report issued Feb. 28, 2012 in International (PCT) Application No. PCT/JP2011/007111.
Supplementary European Search Report issued Jun. 4, 2014 in European Application No. 11850843.1.

* cited by examiner

*Primary Examiner* — Jeffrey S Lundgren
*Assistant Examiner* — William Lee
(74) *Attorney, Agent, or Firm* — Wenderoth, Lind & Ponack, L.L.P.

(57) ABSTRACT

[Problem] To provide a diphenyl sulfide derivative which is useful as a pharmaceutical product that has excellent S1P3 antagonist activity.
[Solution] The inventors have discovered that a diphenyl sulfide derivative represented by general formula (1) (wherein R1 represents an alkoxy group having 1-6 carbon atoms, R2 represents a propyl group or an allyl group, X represents methylene or an oxygen atom, and Z represents a halogen atom) has excellent S1P3 antagonist activity as a result of extensive researches for the production of a compound that has S1P3 antagonist activity.

[Chemical formula 1]

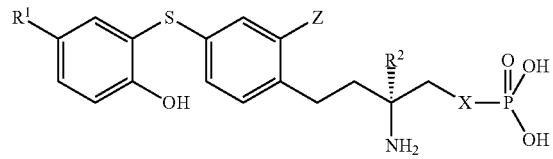

(1)

6 Claims, No Drawings

DIPHENYL SULFIDE DERIVATIVE AND PHARMACEUTICAL PRODUCT WHICH CONTAINS SAME AS ACTIVE INGREDIENT

TECHNICAL FIELD

The present invention relates to a novel diphenyl sulfide derivative that is effective as a medicine, or a pharmaceutically acceptable salt or hydrate thereof, and a sphingosine-1-phosphate (S1P3) receptor-antagonist and a medicine containing the same as an active ingredient.

BACKGROUND ART

Sphingosine-1-phosphate (S1P) was considered to be merely an intermediary metabolite in sphingosine metabolism. However, it has been reported that S1P has a cell growth promoting action and a control action of a cell motility function, and it is now clear that S1P is a new lipid mediator that exhibits various physiological actions, such as an apoptosis action, a cell morphology regulation action, and vasoconstriction (Non-Patent Literatures 1 and 2).

This S1P combines two actions, an action as an intracellular second messenger and an action as an intercellular mediator. Studies into S1P's action as an intercellular mediator are especially active. It has been reported that information is transmitted via a plurality of G protein-coupled receptors present on the cell membrane surface (Endothelial Differentiation Gene, EDG) (Non-Patent Literatures 1 and 3). Currently, five sub-types of S1P receptors are known, including Edg-1, Edg-3, Edg-5, Edg-6, and Edg-8 which are called as $S1P_1$, $S1P_3$, $S1P_2$, $S1P_4$, and $S1P_5$, respectively.

From various studies into these S1P receptors, it has been reported that so-called S1P receptor regulator, which exhibits an agonistic or antagonistic action against this receptor, is effective against a wide range of diseases. Patent Literature 2 and Non-Patent Literatures 4 to 7 report that the S1P3 antagonist is effective as a therapeutic or preventive medicine for respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, sepsis, or cytokine storm caused by an influenza virus or RS virus infection.

Further, Patent Literatures 3 to 6 show that the S1P3 antagonist is also effective against arterial sclerosis, blood vessel intimal hypertrophy, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema such as ARDS, cardiac arrhythmia, eye disease, eye hypertension, glaucoma, glaucomatous retinopathy, optic neuropathy, macula-lutea degeneration and the like.

Further, although currently there are recombinants form of human activated protein C (rhAPC) in medicines that are effective as sepsis therapeutic medicines, rhAPC may also cause hemorrhaging as a side effect. Therefore, there is a need to develop a novel sepsis therapeutic or preventive medicine that does not exhibit such side effects. Non-Patent Literatures 5 and 7 report that the S1P3 receptor contributes to multiple organ failure caused by sepsis based on analysis using S1P3 knockout mice, thereby suggesting that the S1P3 antagonist may be effective as a sepsis therapeutic or preventive medicine. In addition, it has been reported that the S1P1 antagonist increases vascular wall permeability, and causes pulmonary edema (Non-Patent Literature 8). Therefore, in order for a novel sepsis therapeutic or preventive medicine to have a high level of safety, that therapeutic or preventive medicine should have a weak S1P1 antagonistic action, preferably exhibit an S1P1 agonistic action, and more preferably not exhibit an action against the S1P1 receptor.

Known S1P receptor regulators include, for example, the compounds represented by the following general formula (A) described in Patent Literature 1,

[Formula 1]

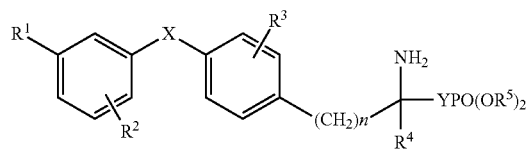

(A)

(In the formula (A), $R^1$ represents a hydrogen atom, a halogen atom, a halogenated or unhalogenated lower alkyl group having 1 to 4 carbon atoms, a hydroxy group, a phenyl group, an aralkyl group, a lower alkoxy group having 1 to 4 carbon atoms, a trifluoromethyloxy group, an optionally substituted aralkyloxy group, an optionally substituted phenoxy group, a cyclohexylmethyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group, or a cyano group; $R^2$ represents a hydrogen atom, a halogen atom, a halogenated or unhalogenated lower alkyl group having 1 to 4 carbon atoms, a lower alkoxy group having 1 to 4 carbon atoms, an aralkyl group, or an aralkyloxy group; $R^3$ represents a hydrogen atom, a halogen atom, a trifluoromethyl group, a lower alkyl group having 1 to 4 carbon atoms, a lower alkoxy group having 1 to 4 carbon atoms, a hydroxy group, a benzyloxy group, a phenyl group, a lower alkoxymethyl group having 1 to 4 carbon atoms or a lower alkylthio group having 1 to 4 carbon atoms; $R^4$ represents a hydrogen atom, a halogen atom, a trifluoromethyl group, a lower alkyl group having 1 to 4 carbon atoms, a lower alkoxymethyl group having 1 to 4 carbon atoms, a lower alkylthiomethyl group having 1 to 4 carbon atoms, a hydroxymethyl group, a phenyl group, or an aralkyl group; $R^5$ represents a hydrogen atom or a lower alkyl group having 1 to 4 carbon atoms; X represents O, S, SO, or $SO_2$; and Y represents —$CH_2O$—, —$CH_2$—, —CH=CH—, —CF=CF—, —$CH_2CH_2$—, —$CH_2CFH$—, —$CH_2CF_2$—, or —$CH(OH)CF_2$—.).

However, Patent Literature 1 does not include 2-aminophosphoric acid monoester derivatives or 3-aminophosphonic acid derivatives having a diphenyl sulfide skeleton in which a hydroxyl group is substituted for a phenyl group. Further, the fact that 2-aminophosphoric acid monoester derivatives or 3-aminophosphonic acid derivatives having such a structure exhibit an excellent S1P3 receptor-antagonistic action is also not known.

Other examples of known S1P receptor regulators include the compounds represented by the following general formula (B) in Patent Literature 6,

[Formula 2]

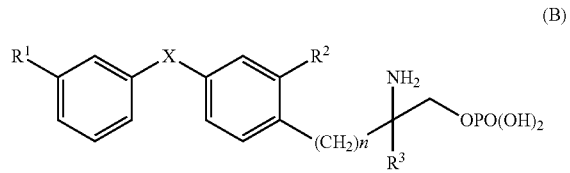

(In the formula (B), $R^1$ represents a chlorine atom, a linear alkyl group having 1 to 3 carbon atoms, or a trifluoromethyl group; $R^2$ represents a fluorine atom or a chlorine atom; $R^3$ represents a linear alkyl group having 1 to 3 carbon atoms; X represents an oxygen atom or a sulfur atom; and n denotes an integer of 2 or 3.).

Further, among the compounds represented by the general formula (B), it has been reported that the optically active compounds represented by the general formula (Ba).

[Formula 3]

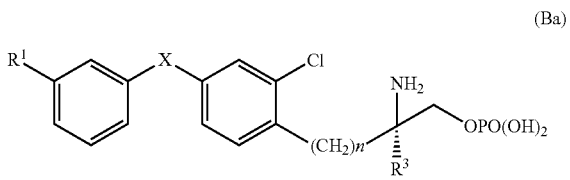

(In the formula (Ba), $R^1$, $R^3$, and X are as defined above.)

It has been reported that the optically active compounds represented by the general formula (Ba) have a weak S1P3 agonistic action and an excellent agonistic action against S1P1 and/or S1P4. However, the compounds having an inverse asymmetric center to the optically active compounds represented by the general formula (Ba), are not known. Further, the fact that such optically active compounds exhibit an excellent S1P3 receptor-antagonistic action is also not known.

Patent Literature 1 WO04074297 pamphlet
Patent Literature 2 WO03020313 pamphlet
Patent Literature 3 Japanese Patent Application Laid-Open No. 2005-247691
Patent Literature 4 WO07043568 pamphlet
Patent Literature 5 WO06063033 pamphlet
Patent Literature 6 WO08018427 pamphlet
Non-Patent Literature 1 Y. Takuma et al., Mol. Cell. Endocrinol., 177, 3 (2001).
Non-Patent Literature 2 Y. Igarashi, Ann, N.Y. Acad. Sci., 845, 19 (1998).
Non-Patent Literature 3 H. Okazaki et al., Biochem. Biophs. Res. Commun., 190, 1104 (1993).
Non-Patent Literature 4 Y. Gon et. al., Proc Natl Acad Sci USA. 102(26), 9270 (2005).
Non-Patent Literature 5 F. Nissen et al., Nature, 452, 654 (2008)
Non-Patent Literature 6 D. Christina et al., Am. J. Pathol., 170(1), 281 (2007)
Non-Patent Literature 7 F. Nissen et al., Blood, 113(12), 2859 (2009)
Non-Patent Literature 8 M. G. Sanna et al., Nature Chemical biology, 2, 434 (2006)

SUMMARY OF THE INVENTION

Problems to be Solved by the Invention

It is an object of the present invention to provide a diphenyl sulfide derivative having an excellent S1P3 antagonistic activity.

Means for Solving the Problems

As a result of intensive studies into the S1P3 antagonist, the present inventors discovered that a novel diphenyl sulfide derivative has an excellent S1P3 antagonistic action, thereby completing the present invention.

Specifically, a first aspect of the invention relates to a diphenyl sulfide derivative, or a pharmaceutically acceptable salt or hydrate thereof, represented by the general formula (1).

[Chemical formula 4]

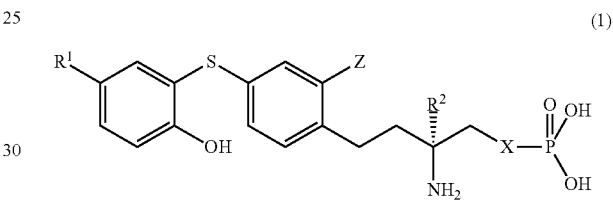

(In the formula (1), $R^1$ represents an alkoxy group having 1 to 6 carbon atoms, $R^2$ represents a propyl group or an allyl group, X represents methylene or an oxygen atom, and Z represents a halogen atom.)

Further, a second aspect of the invention relates to the diphenyl sulfide derivative according to the first aspect of the invention, or a pharmaceutically acceptable salt or hydrate thereof, wherein the compound represented by the general formula (1) is represented by the general formula (1a).

[Chemical formula 5]

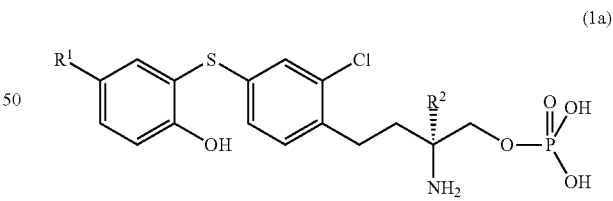

(In the formula (Ia), $R^1$ and $R^2$ are as defined in the first aspect of the invention.)

A third aspect of the invention relates to the diphenyl sulfide derivative according to the first aspect of the invention, or a pharmaceutically acceptable salt or hydrate thereof, wherein the compound represented by the general formula (1) is an (R)-2-allyl-2-amino-4-{2-chloro-4-(5-ethoxy-2-hydroxyphenylthio)phenyl}butylphosphoric acid monoester or an (S)-2-amino-4-{2-chloro-4-(5-ethoxy-2-hydroxyphenylthio)phenyl}-2-propylbutylphosphoric acid monoester.

A fourth aspect of the invention relates to a medicine that comprises the diphenyl sulfide derivative according to any one of the first to third aspects of the invention, or a pharmaceutically acceptable salt or hydrate thereof.

In addition, a fifth aspect of the invention relates to the medicine according to the fourth aspect of the invention, wherein the medicine is a therapeutic or preventive medicine for respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, sepsis, or cytokine storm caused by an influenza virus or RS virus infection.

Still further, a sixth aspect of the invention relates to the medicine according to the fourth aspect of the invention, wherein the medicine is a therapeutic or preventive medicine for arteriosclerosis, blood vessel intimal thickening, solid tumors, diabetic retinopathy, articular rheumatism, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema, cardiac arrhythmia, eye disease, eye hypertension, glaucoma, glaucomatous retinopathy, optic neuropathy, or macula-lutea degeneration.

Further, a seventh aspect of the invention relates to the medicine according to the fourth aspect of the invention, wherein the medicine is a therapeutic or preventive medicine for sepsis.

In addition, an eighth aspect of the invention relates to a pharmaceutical composition comprising the diphenyl sulfide derivative according to any one of the first to third aspects of the invention, or a pharmaceutically acceptable salt or hydrate thereof, and a pharmaceutically acceptable carrier.

Advantageous Effects of Invention

According to the present invention, a diphenyl sulfide derivative having an excellent S1P3 antagonistic action and S1P3 selectivity can be provided. Further, the diphenyl sulfide derivative of the present invention can be safely used as a medicine, as it causes little or no hemolysis, tissue damage, or central depressant action. In addition, the diphenyl sulfide derivative of the present invention is stable in aqueous solution. The compound of the present invention having these excellent properties is effective as a preventive or a therapy for sepsis, respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, cytokine storm (hyperproduction) caused by an influenza virus or RS virus infection, arteriosclerosis, bloodvessel intimal thickening, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema such as ARDS, cardiac arrhythmia, eye disease, eye hypertension, glaucoma, glaucomatous retinopathy, optic neuropathy, and macula-lutea degeneration.

MODE FOR CARRYING OUT THE INVENTION

In the following description the definition of the functional groups in the general formulae may be omitted by referring to an already-provided definition. These referral definitions refer to a definition provided in the following description of the embodiments. It should naturally be understood that these referral definitions do not refer to the definitions of the functional groups on the compounds mentioned as prior art.

The "halogen atom" used in the present invention is a fluorine atom, a chlorine atom, a bromine atom, or an iodine atom. Examples of the "alkoxy group having 1 to 6 carbon atoms" include a methoxy group, an ethoxy group, an n-propoxy group, an n-butoxy group, an i-propoxy group, and a t-butoxy group.

Further, in the present invention, to obtain an excellent S1P3 antagonistic action and for a safety for a living body, it is preferred that $R^1$ be an alkoxy group having 1 to 6 carbon atoms, and an ethoxy group is especially preferred.

In addition, it is preferred that $R^2$ be a propyl group or an allyl group.

Still further, it is preferred that X be methylene or an oxygen atom, and an oxygen atom is especially preferred.

Furthermore, it is preferred that Z be a halogen atom, and a chlorine atom is especially preferred.

Examples of a pharmaceutically acceptable salt in the present invention include an acid addition salt, such as a hydrochloride salt, a hydrobromide salt, an acetate salt, a trifluoroacetate salt, a methanesulfonate salt, a citrate salt, or a tartrate salt, and an alkaline addition salt, such as a sodium salt, a potassium salt, a calcium salt, a magnesium salt, or an aluminum salt.

Among the compounds represented by the general formula (1), a compound in which X is an oxygen atom, specifically, a compound represented by the general formula (Id), can be prepared based on the following synthesis pathway A, for example.

[Formula 6]

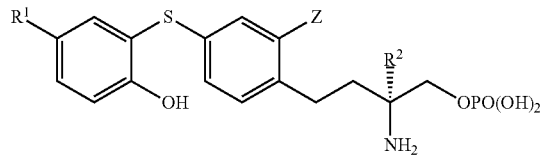

(Id)

(In the formula (Id), $R^1$ represents an alkoxy group having 1 to 6 carbon atoms, $R^2$ represents a propyl group or an allyl group, and Z represents a halogen atom.)<

<Synthesis Pathway A>

[Formula 7]

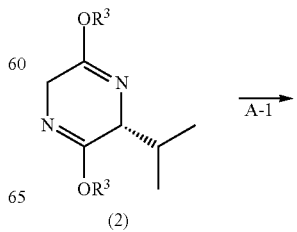

(2)

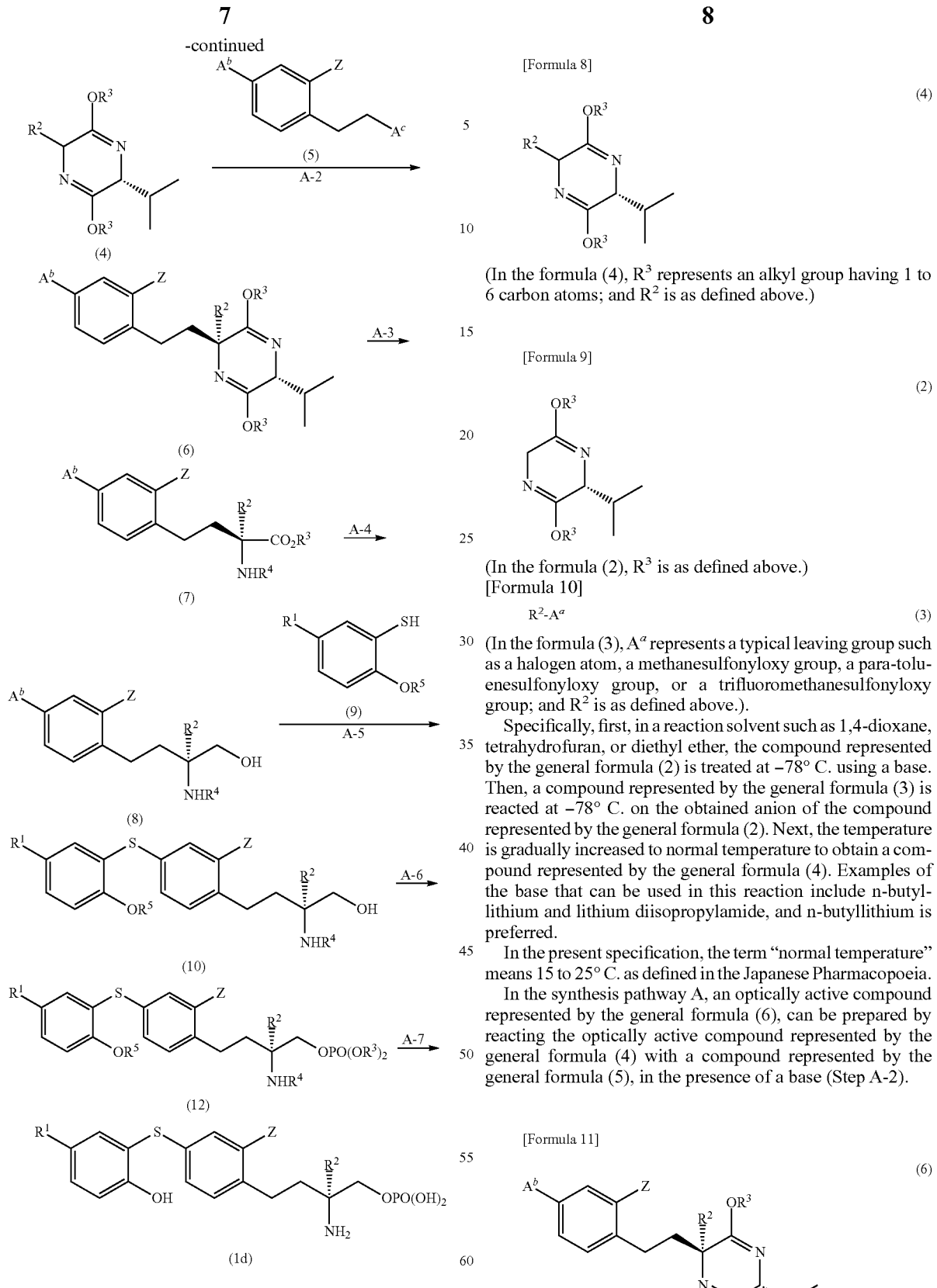

(In the formula (4), $R^3$ represents an alkyl group having 1 to 6 carbon atoms; and $R^2$ is as defined above.)

[Formula 9]

(2)

(In the formula (2), $R^3$ is as defined above.)
[Formula 10]

$$R^2-A^a \quad (3)$$

(In the formula (3), $A^a$ represents a typical leaving group such as a halogen atom, a methanesulfonyloxy group, a para-toluenesulfonyloxy group, or a trifluoromethanesulfonyloxy group; and $R^2$ is as defined above.).

Specifically, first, in a reaction solvent such as 1,4-dioxane, tetrahydrofuran, or diethyl ether, the compound represented by the general formula (2) is treated at −78° C. using a base. Then, a compound represented by the general formula (3) is reacted at −78° C. on the obtained anion of the compound represented by the general formula (2). Next, the temperature is gradually increased to normal temperature to obtain a compound represented by the general formula (4). Examples of the base that can be used in this reaction include n-butyllithium and lithium diisopropylamide, and n-butyllithium is preferred.

In the present specification, the term "normal temperature" means 15 to 25° C. as defined in the Japanese Pharmacopoeia.

In the synthesis pathway A, an optically active compound represented by the general formula (6), can be prepared by reacting the optically active compound represented by the general formula (4) with a compound represented by the general formula (5), in the presence of a base (Step A-2).

[Formula 11]

(6)

(In the formula (6), $A^b$ represents a typical leaving group such as a halogen atom, a methanesulfonyloxy group, a para-tolu- In the synthesis pathway A, an optically active compound represented by the general formula (4), can be prepared by reacting an optically active compound represented by the general formula (2), with a compound represented by the general formula (3), in the presence of a base (Step A-1).

enesulfonyloxy group, or a trifluoromethanesulfonyloxy group; and $R^2$, $R^3$, and Z are as defined above.)

[Formula 12]

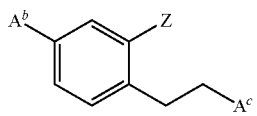

(5)

(In the formula (5), $A^c$ represents a typical leaving group such as a halogen atom, a methanesulfonyloxy group, a para-toluenesulfonyloxy group, or a trifluoromethanesulfonyloxy group; and $A^b$ and Z are as defined above.)

Specifically, first, in a reaction solvent such as 1,4-dioxane, tetrahydrofuran, or diethyl ether, the compound represented by the general formula (4) is treated at −78° C. using a base. Then, the compound represented by the general formula (5) is reacted at −78° C. on the obtained anion of the compound represented by the general formula (4). Next, the temperature is gradually increased to normal temperature to obtain the compound represented by the general formula (6). Examples of the base that can be used in this reaction include n-butyllithium and lithium diisopropylamide, and n-butyllithium is preferred.

In the synthesis pathway A, a compound represented by the general formula (7), can be prepared by subjecting the compound represented by the general formula (6) to acid hydrolysis, and then protecting the amino group with a typical protecting reagent.

[Formula 13]

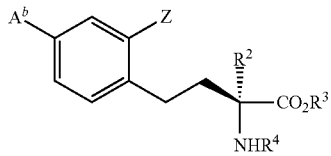

(7)

(In the formula (7), $R^4$ represents a general protecting group for amino group; and $A^b$, $R^2$, $R^3$, and Z are as defined above.)

The $R^4$ in the formula (7) is not especially limited as long as it protects the amino group. For example, an acyl group, such as an acetyl group, or a carbamate, such as t-butoxycarbonyl or benzyloxycarbonyl, can be used (Step A-3).

Specifically, first, in an inorganic or organic acid, or in a mixed solution of an inorganic or organic acid and water or an organic solvent, a compound represented by the general formula (6) is subjected to acid hydrolysis at normal temperature. Here, as the inorganic acid, hydrochloric acid, hydrobromic acid or the like can be used. As the organic acid, trifluoroacetic acid or the like can be used. Further, as the organic solvent, methanol, ethanol, tetrahydrofuran, 1,4-dioxane, ethyl acetate or the like can be used. Among these, it is preferred to carry out the acid hydrolysis using a trifluoroacetic acid aqueous solution.

Next, after neutralization with a base to obtain an amino ester, this amino ester and an acyl chloride or an acid anhydride are reacted at 0° C. to normal temperature in a solvent to obtain the compound represented by the general formula (7). Examples of the solvent that can be used in this step include ethyl acetate, tetrahydrofuran, N,N-dimethylformamide, 1,4-dioxane, methylene chloride, chloroform, methanol, ethanol, and acetonitrile. As the acyl chloride, acetyl chloride, benzyloxycarbonyl chloride or the like can be used. As the acid anhydride, acetic anhydride, di-t-butyldicarbonate or the like can be used. Among these, it is preferred to carry out the reaction using di-t-butyldicarbonate.

In the synthesis pathway A, a compound represented by the general formula (8) can be prepared by reducing the compound represented by the general formula (7) (Step A-4).

[Formula 14]

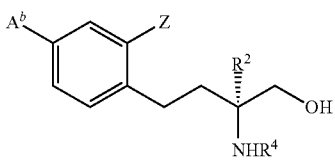

(8)

(In the formula (8), $A^b$, $R^2$, $R^4$, and Z are as defined above.)

For example, in a reaction solvent such as tetrahydrofuran, 1,4-dioxane, ethanol, methanol or the like, the compound represented by the general formula (7) is redused using a reductant at 0° C. to the reflux temperature, and preferably at normal temperature. Examples of the reductant that can be used include borane, alkyl borane derivatives such as 9-borabicyclo[3.3.1]nonane (9-BBN), metal hydride complexes such as diisobutylaluminum hydride ($(iBu)_2AlH$), sodiumborohydride ($NaBH_4$), lithiumborohydride ($LiBH_4$), lithium aluminum hydride ($LiAlH_4$) or the like. Preferably, the reductant is lithium borohydride.

In the synthesis pathway A, a compound represented by the general formula (10), can be prepared by reacting the compound represented by the general formula (8) and the compound represented by the general formula (9).

[Formula 15]

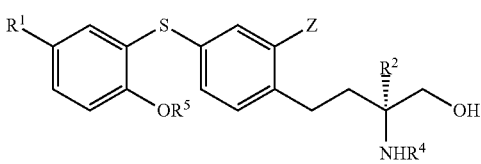

(10)

(In the formula (10), $R^5$ represents a hydrogen atom or a general protecting group for a phenolic hydroxyl group; and $R^1$, $R^2$, $R^4$, and Z are as defined above.)

[Formula 16]

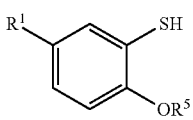

(9)

(In the formula (9), $R^1$ and $R^5$ are as defined above.)

The general protecting group for a phenolic hydroxyl group is not especially limited as long as it protects a phenolic hydroxyl group. For example, a methyl group, a benzyl group, a methoxymethyl group, a tetrahydropyranyl group, a t-butyldimethylsilyl group, an acetyl group, or a t-butoxycarbonyl group can be used (Step A-5).

For example, this reaction can be carried out in a reaction solvent, such as toluene, N,N-dimethylformamide, 1,4-dioxane, tetrahydrofuran, or diethyl ether, in the presence of an inorganic or organic base using a catalyst at normal temperature to the reflux temperature. Examples of inorganic bases that can be used include sodium carbonate or potassium t-butoxide. Examples of organic bases that can be used include diisopropyethylamine. Further, examples of the catalyst that can be used include palladium compounds, such as tris(dibenzylideneacetone) dipalladium(0) or palladium(II) acetate. Preferably, tris(dibenzylideneacetone) dipalladium(0) is used.

A phosphine compound, such as 4,5-bis(diphenylphosphino)-9,9-dimethylxanthene, bis[2-(diphenylphosphino)phenyl]ether, or 1,1'-bis(di-t-butyl phosphino)ferrocene, may be added to the reaction solvent as a reaction accelerator.

In the synthesis pathway A, a compound represented by the general formula (12), can be prepared by reacting the compound represented by the general formula (10) and a compound represented by the general formula (11) (Step A-6).

[Formula 17]

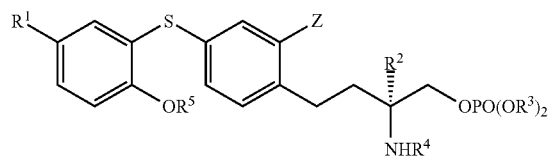

(12)

(In the formula (12), $R^1$, $R^2$, $R^3$, $R^4$, $R^5$, and Z are as defined above.),

[Formula 18]

(11)

(In the formula (11), $R^3$ is as defined above.)

For example, this reaction can be carried out in the presence of carbon tetrabromide and pyridine, using no solvent or a solvent such as methylene chloride, chloroform, acetonitrile, ethyl acetate, tetrahydrofuran, or diethyl ether, at 0° C. to normal temperature.

In the synthesis pathway A, a compound represented by the general formula (1d) can be prepared by subjecting the compound represented by the general formula (12) to acid hydrolysis or treatment with a nucleophilic reagent, such as trimethylsilyl bromide or trimethylsilyl iodide (Step A-7).

For the acid hydrolysis reaction, acid hydrolysis can be carried out in an inorganic acid such as hydrochloric acid or hydrobromic acid, or in a mixed solution of an organic solvent such as methanol or ethanol and an inorganic acid, at the reflux temperature. Further, a treatment using a nucleophilic reagent can be carried out by reacting trimethylsilyl bromide or trimethylsilyl iodide at 0° C. to normal temperature using acetonitrile or methylene chloride as a preferred reaction solvent. Alternatively, the treatment with a nucleophilic reagent can also be carried out by reacting with a combination of trimethylsilyl chloride and sodium bromide or a combination of trimethylsilyl chloride and sodium iodide.

In the synthesis pathway A, the compound represented by the general formula (7) can also be prepared based on the following synthesis pathway B, for example.

<Synthesis Pathway B>

[Formula 19]

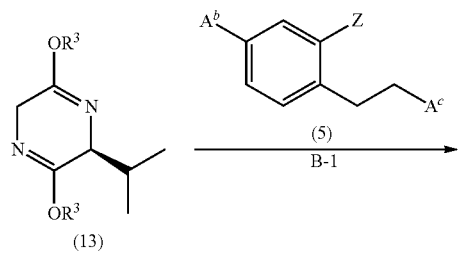

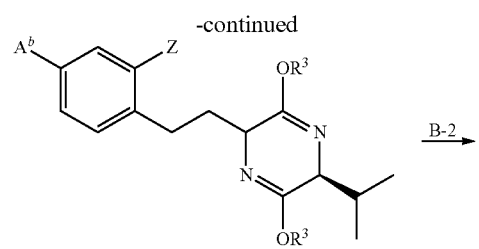

(14)

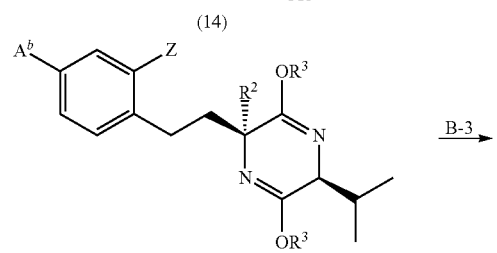

(15)

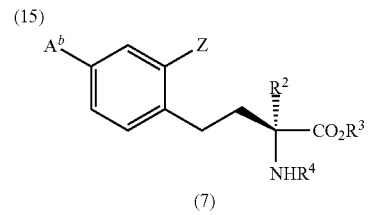

(7)

In the synthesis pathway B, an optically active compound represented by the general formula (14), can be prepared based on the same method as in Step A-2 using an optically active compound represented by the general formula (13), and the compound represented by the general formula (5) (Step B-1).

[Formula 20]

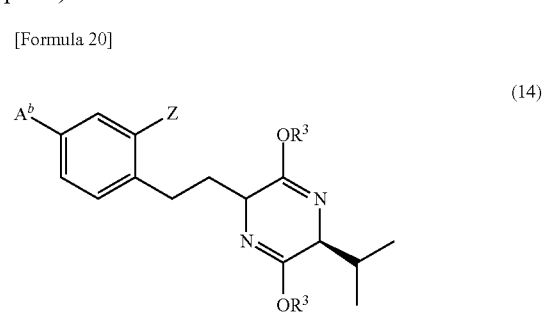

(14)

(In the formula (14), $A^b$, $R^3$, and Z are as defined above.),

[Formula 21]

(13)

(In the formula (13), $R^3$ is as defined above.)

In the synthesis pathway B, an optically active compound represented by the general formula (15), can be prepared based on the same method as in Step A-1 using the optically active compound represented by the general formula (14) and the compound represented by the general formula (3) (Step B-2).

[Formula 22]

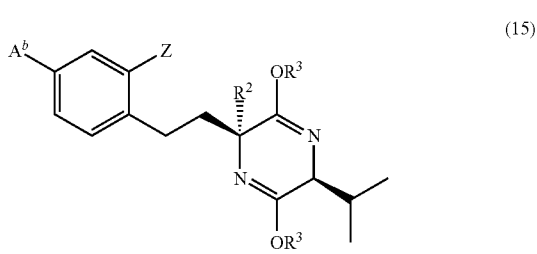

(In the formula (15), $A^b$, $R^2$, $R^3$, and Z are as defined above.)

In the synthesis pathway B, the compound represented by the general formula (7) can be prepared based on the same method as in Step A-3 using the compound represented by the general formula (15) (Step B-3).

In the synthesis pathway A, the compound represented by the general formula (10) can be prepared based on the following synthesis pathway C, for example.

<Synthesis Pathway C>

[Formula 23]

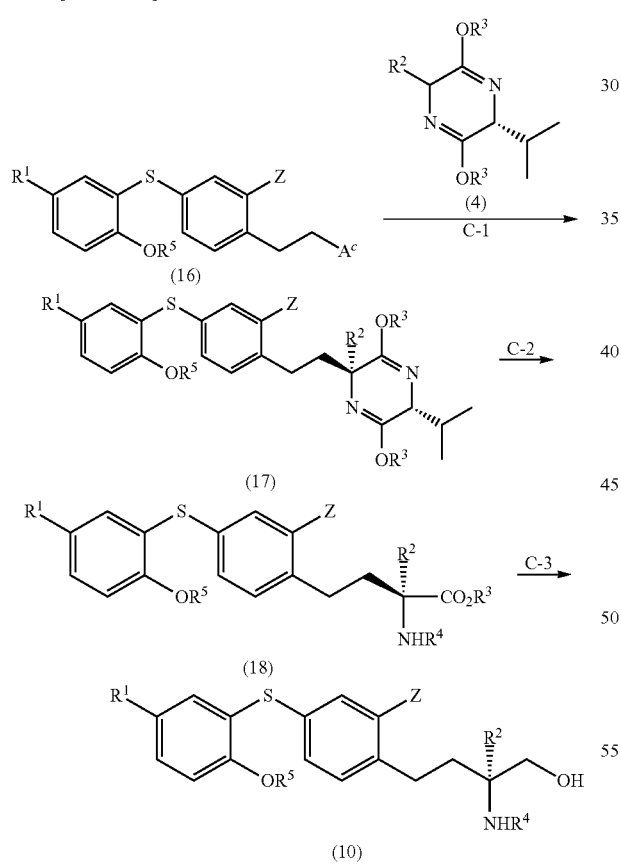

In the synthesis pathway C, an optically active compound represented by the general formula (17), can be prepared based on the same method as in Step A-2 using the optically active compound represented by the general formula (4) and a compound represented by the general formula (16) (Step C-1).

[Formula 24]

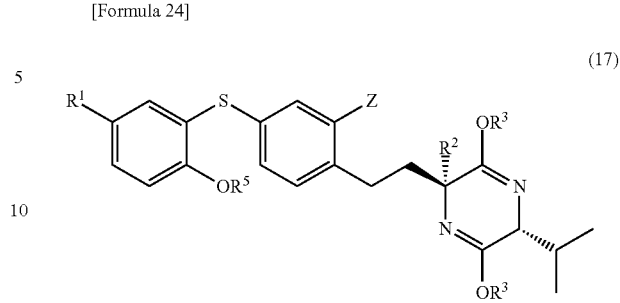

(In the formula (17), $R^1$, $R^2$, $R^3$, $R^5$, and Z are as defined above.)

[Formula 25]

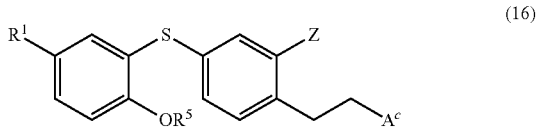

(In the formula (16), $R^1$, $R^5$, $A^c$, and Z are as defined above.)

In the synthesis pathway C, a compound represented by the general formula (18), can be prepared based on the same method as in Step A-3 using the compound represented by the general formula (17) (Step C-2).

[Formula 26]

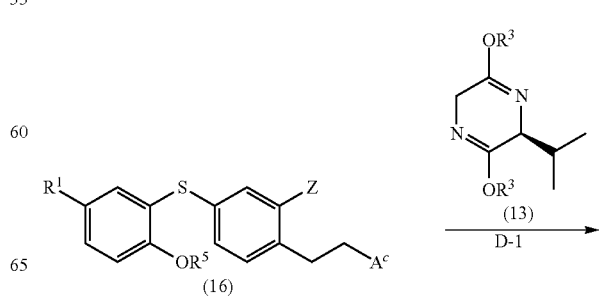

(In the formula (18), $R^1$, $R^2$, $R^3$, $R^4$, $R^5$, and Z are as defined above.)

In the synthesis pathway C, the compound represented by the general formula (10) can be prepared based on the same method as in Step A-4 using the compound represented by the general formula (18) (Step C-3).

In the synthesis pathway C, the compound represented by the general formula (18) can be prepared based on the following synthesis pathway D, for example.

<Synthesis Pathway D>

[Formula 27]

-continued

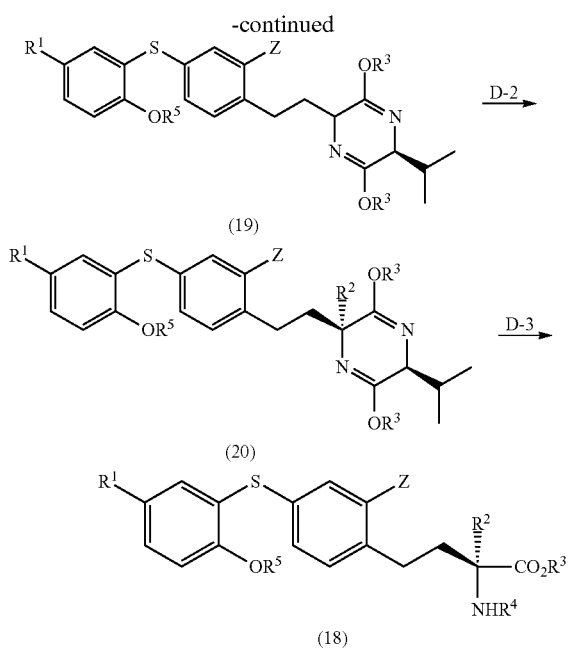

In the synthesis pathway D, an optically active compound represented by the general formula (19), can be prepared based on the same method as in Step A-2 using the optically active compound represented by the general formula (13) and the compound represented by the general formula (16) (Step D-1).

[Formula 28]

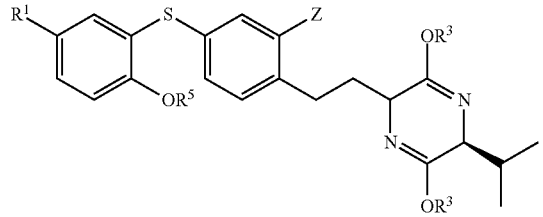

(In the formula (19), $R^1$, $R^3$, $R^5$, and Z are as defined above.)

In the synthesis pathway D, an optically active compound represented by the general formula (20), can be prepared based on the same method as in Step A-1 using the optically active compound represented by the general formula (19) and the compound represented by the general formula (3) (Step D-2).

[Formula 29]

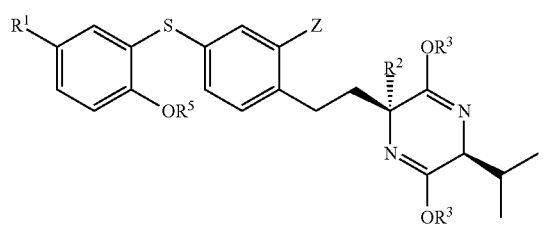

(In the formula (20), $R^1$, $R^2$, $R^3$, $R^5$, and Z are as defined above.)

In the synthesis pathway D, the compound represented by the general formula (18) can be prepared based on the same method as in Step A-3 using the compound represented by the general formula (20) (Step D-3).

In the synthesis pathway A, among the compounds represented by the general formula (10), a compound in which $R^1$ is a cyano group or an acetyl group and $R^5$ is a general protecting group for phenol, specifically, a compound represented by the general formula (10a), can be prepared by the following synthesis pathway E, for example.

[Formula 30]

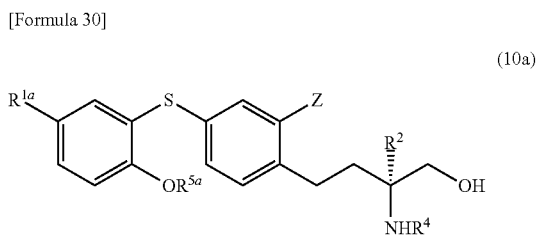

(In the formula (10a), $R^{1a}$ represents an acetyl group or a cyano group and $R^{5a}$ represents a general protecting group for a phenolic hydroxyl group; and $R^2$, $R^4$, and Z are as defined above.)

$R^{5a}$ is not especially limited, as long as it protects a phenolic hydroxyl group. For example, a methyl group, a benzyl group, a methoxymethyl group, a tetrahydropyranyl group, a t-butyldimethylsilyl group, an acetyl group, or a t-butoxycarbonyl group can be used.

<Synthesis Pathway E>

[Formula 31]

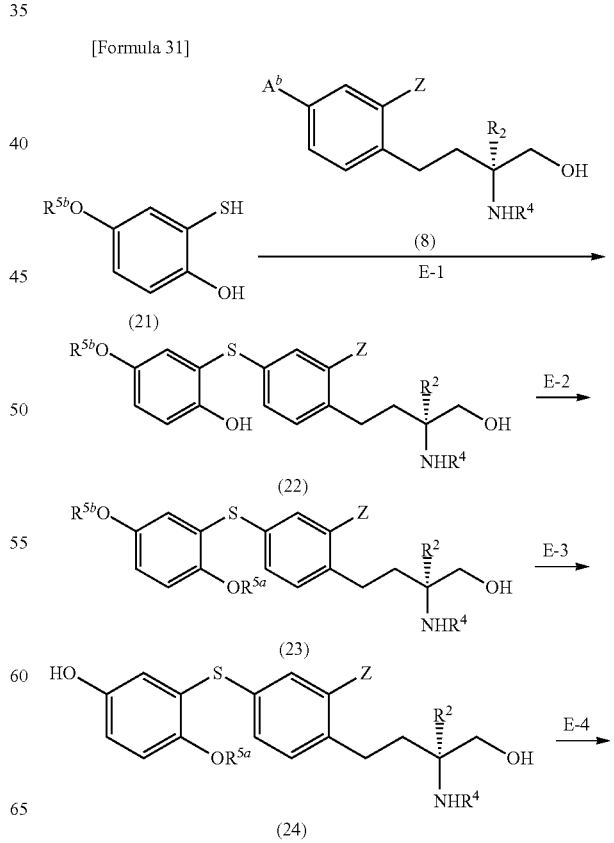

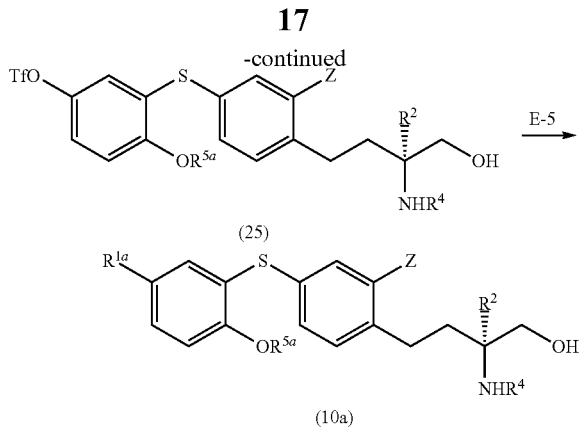

(25)

(10a)

In the synthesis pathway E, an optically active compound represented by the general formula (22), can be prepared based on the same method as in Step A-5 using the optically active compound represented by the general formula (8) and a compound represented by the general formula (21).

[Formula 32]

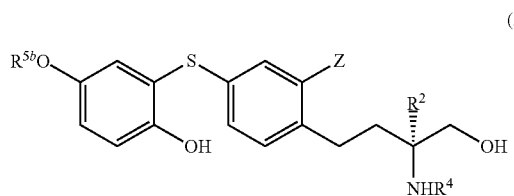

(22)

(In the formula (22), $R^{5b}$ represents a general protecting group for a phenolic hydroxyl group; and $R^2$, $R^4$, and Z are as defined above.)

[Formula 33]

(21)

(In the formula (21), $R^{5b}$ is as defined above.)

$R^{5b}$ is not especially limited, as long as it protects a phenolic hydroxyl group. For example, a methyl group, a benzyl group, a methoxymethyl group, a tetrahydropyranyl group, a t-butyldimethylsilyl group, an acetyl group, or a t-butoxycarbonyl group can be used (Step E-1).

In the synthesis pathway E, a compound represented by the general formula (23), can be prepared by protecting the phenolic hydroxyl group of the compound represented by the general formula (22) (Step E-2).

[Formula 34]

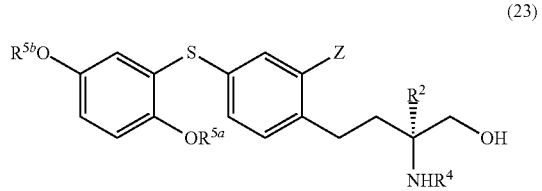

(23)

(In the formula (23), $R^2$, $R^4$, $R^{5a}$, $R^{5b}$, and Z are as defined above.)

This reaction can be carried out by any technique that is commonly used to protect a phenolic hydroxyl group. For example, the reaction can be carried out in a solvent such as acetonitrile, tetrahydrofuran, N,N-dimethylformamide, methylene chloride, or chloroform, in the presence of an inorganic or organic base, by reacting a compound represented by the general formula (22) with a chloride or an acyl chloride. As the inorganic base, potassium carbonate or the like can be used. As the organic base, triethylamine, diisopropylethylamine or the like can be used. Further, examples of the chloride that can be used include methoxymethyl chloride, t-butyldimethylsilyl chloride, and benzyl chloride. Examples of the acyl chloride that can be used include acetyl chloride. Among these, it is preferred to protect the phenolic hydroxyl group using methoxymethyl chloride. In addition, the reaction can be carried out by reacting at 0° C. to normal temperature.

In the synthesis pathway E, a compound represented by the general formula (24), can be prepared by removing the $R^{5b}$ in the compound represented by the general formula (23) (Step E-3).

[Formula 35]

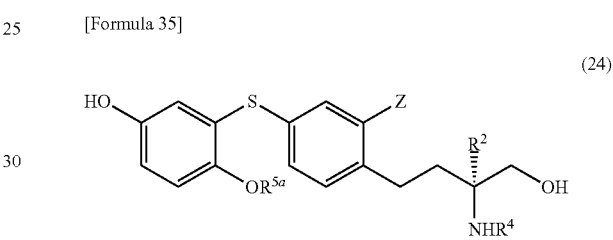

(24)

(In the formula (24), $R^2$, $R^4$, $R^{5a}$, and Z are as defined above.)

The reaction is not especially limited, as long as the technique is commonly used to remove a protecting group for a phenolic hydroxyl group, and $R^{5a}$ is not removed. An example will be described in which $R^{5b}$ is a silyl protecting group, such as a t-butyldimethylsilyl group. In this case, the deprotection reaction can be carried out in a reaction solvent such as tetrahydrofuran, acetonitrile, or methylene chloride using a fluorine compound, such as tetrabutylammonium fluoride or hydrogen fluoride-pyridine, and preferably tetrabutylammonium fluoride. This deprotection reaction can be carried out at from 0° C. to the reflux temperature, and preferably at 0° C.

In the synthesis pathway E, a compound represented by the general formula (25), can be prepared by reacting the compound represented by the general formula (24) with N-phenyltrifluoromethanesulfonimide (Step E-4).

[Formula 36]

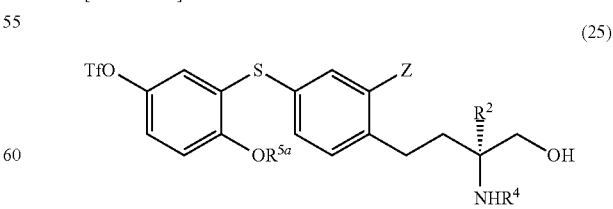

(25)

(In the formula (25), $R^2$, $R^4$, $R^{5a}$, and Z are as defined above.)

For example, this reaction can be carried out by reacting with N-phenyltrifluoromethanesulfonimide in the presence of an organic base such as pyridine, triethylamine or the like using a solvent such as methylene chloride, chloroform, toluene or the like at 0° C. to 80° C., and preferably at normal temperature.

In the synthesis pathway E, a compound represented by the general formula (10a) can be prepared based on a known method using zinc cyanide (e.g., Synth. Commun., 25, 3255-3261 (1995)), or a known method using a Heck reaction (e.g., J. Org., Chem., 55, 3654-3655 (1990)) from a compound represented by the general formula (25) (Step E-5).

An example will be described in which $R^{1a}$ is a cyano group. In this case, the reaction can be carried out in the presence of zinc cyanide, in a reaction solvent such as toluene, N,N-dimethylformamide, 1,4-dioxane, tetrahydrofuran, or the like using a catalyst at normal temperature to the reflux temperature. Examples of catalysts that can be used include palladium compounds such as tetrakistriphenylphosphine palladium(0) or tris (dibenzylideneacetone) dipalladium(0), and preferably tetrakistriphenylphosphine palladium(0). Further, a phosphine compound, such as 1,1'-bis(diphenylphosphino)-ferrocene or 1,3-bis(diphenylphosphino)-propane, may be added to the reaction solvent as a reaction accelerator.

Another example will be described in which $R^{1a}$ is an acetyl group. In this case, the reaction can be carried out in the presence of an organic base, using a catalyst and a reaction accelerator, in a solvent such as toluene, N,N-dimethylformamide, 1,4-dioxane, tetrahydrofuran or the like, by reacting with butyl vinyl ether. As the organic base, triethylamine, diisopropylethylamine or the like can be used. Further, as the catalyst, palladium (II) acetate can be used. As the reaction accelerator, 1,3-bis(diphenylphosphino)-propane may be used. The reaction can be carried out at normal temperature to the reflux temperature.

Among the compounds represented by the general formula (1), a compound in which X is methylene, specifically, a compound represented by the general formula (1e), can be prepared based on the following synthesis pathway F, for example.

[Formula 37]

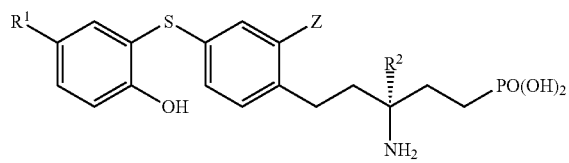

(1e)

(In the formula (1e), $R^1$, $R^2$, and Z are as defined above.)

<Synthesis Pathway F>

[Formula 38]

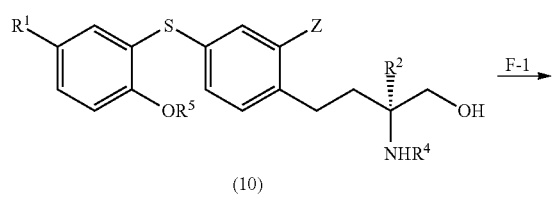

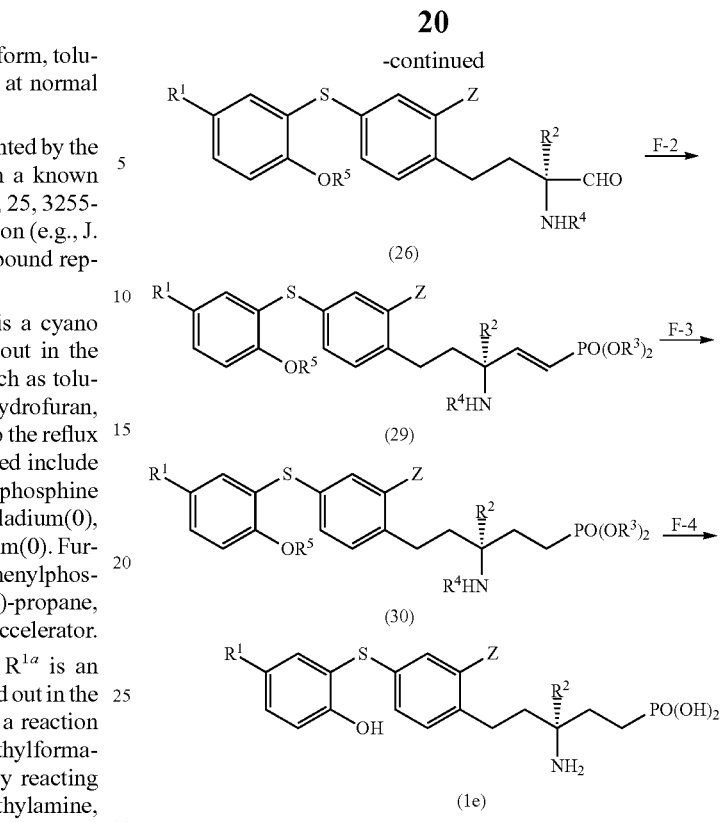

In the synthesis pathway F, a compound represented by the general formula (26), can be prepared by oxidation of the compound represented by the general formula (10) (Step F-1).

[Formula 39]

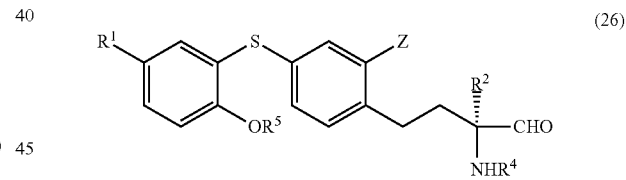

(In the formula (26), $R^1$, $R^2$, $R^4$, $R^5$, and Z are as defined above.)

This reaction can be carried out using a generally used oxidation method to generate aldehyde from alcohol. Examples of this oxidation treatment may include an oxidation treatment that uses a chromium oxide-pyridine complex such as pyridinium chlorochromate or pyridinium dichromate, or oxidation that uses hypervalent iodine such as Dess-Martin oxidation. Alternatively, dimethyl sulfoxide oxidation using various dimethyl sulfoxide activating agents, such as oxalyl chloride, trifluoroacetic anhydride, acetic anhydride, dicyclohexylcarbodiimide, or a sulfur trioxide-pyridine complex, may be used.

In the synthesis pathway F, a compound represented by the general formula (29) can be prepared by, for example, reacting the compound represented by the general formula (26) and a compound represented by the general formula (27), in a reaction solvent in the presence of a base.

[Formula 40]

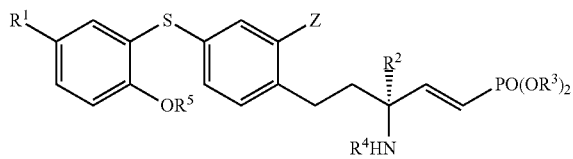

(29)

(In the formula (29), $R^1$, $R^2$, $R^3$, $R^4$, $R^5$, and Z are as defined above.)

[Formula 41]

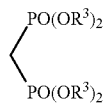

(27)

(In the formula (27), $R^3$ is as defined above.)

Examples of the base that can be used in this reaction include sodium hydride, potassium hydride, sodium alkoxide, potassium alkoxide, or n-butyllithium, and preferably n-butyllithium. As the reaction solvent, tetrahydrofuran, diethyl ether, or 1,4-dioxane may be used. Further, the reaction temperature may be set to −78° C. to normal temperature.

In the synthesis pathway F, a compound represented by the general formula (30), can be prepared by reducing a compound represented by the general formula (29) (Step F-3).

[Formula 42]

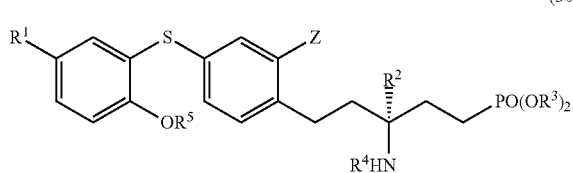

(30)

(In the formula (30), $R^1$, $R^2$, $R^3$, $R^4$, $R^5$, and Z are as defined above.)

For example, this reaction can be carried out in the presence of a catalyst for catalytic hydrogenation, in a solvent such as ethanol, methanol, tetrahydrofuran, N,N-dimethylformamide, or ethyl acetate, under a normal pressure to increased hydrogen pressure at normal temperature. Examples of catalysts for catalytic hydrogenation that can be used include palladium carbon, platinum carbon, platinum oxide, rhodium carbon, or ruthenium carbon.

Further, this reaction can also be carried out by diimide reduction. For example, the reaction can be carried out using potassium azodicarboxylate in thepresence of acetic acid in a solvent such as pyridine, ethanol, methanol, dimethylsulfoxide, or 1,4-dioxane at a temperature of from normal temperature to heating to reflux.

In the synthesis pathway F, a compound represented by the general formula (1e) can be prepared based on the same method as in Step A-7 using the compound represented by the general formula (30) (Step F-4).

Further, the synthesis method of the compound represent by the general formula (16) can be carried out based on the method described in WO 03029184, WO 03029205, WO 04026817, WO 04074297, and WO 050444780 pamphlets.

The diphenyl sulfide derivative, or a pharmaceutically acceptable salt or hydrate thereof, of the present invention, exhibits an excellent S1P3 antagonistic action, and can be used to produce a medicine based on a sphingosine 1-phosphoric acid 3 (S1P3) receptor-antagonistic action. Morespecifically, amedicine having at least one kind or more of such compounds as an active ingredient is effective as a therapeutic or preventive medicine for diseases for which it is known that an S1P3 antagonist is an effective therapeutic or preventive medicine. Examples of diseases for which it is known that an S1P3 antagonist is an effective therapeutic or preventive medicine include sepsis, respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, or cytokine storm caused by an influenza virus or RS virus infection.

Further, other than the above-described diseases, the medicine of the present invention is also effective for therapy or prevention for diseases for which it is known that an S1P3 antagonistic action is effective. Examples of diseases for which it is known that an S1P3 antagonistic action is effective include arteriosclerosis, bloodvessel intimal thickening, solid tumors, diabetic retinopathy, rheumatoid arthritis, cardiac arrest, ischemia-reperfusion disorders, cerebral bloodvessel spasms after subarachnoid bleeding, angina pectoris or myocardial infarction caused by coronary vessel spasms, glomerulonephritis, thrombosis, lung disease caused by pulmonary edema such as ARDS, cardiac arrhythmia, eye disease, eye hypertension, glaucoma, glaucomatous retinopathy, optic neuropathy, and macula-lutea degeneration.

The medicine of the present invention can be orally administered. Alternatively, the medicine of the present invention can also be administered via a non-oral route, such as intrarectally, subcutaneously, intravenously, intramuscularly, or transdermally.

To use as a medicine, the compound of the present invention, or a pharmaceutically acceptable salt or hydrate thereof, may be in the form of a solid composition, a liquid composition, or some other compositions. The optimum form is selected as necessary. The pharmaceutical composition of the present invention can be prepared by mixing the compound of the present invention with a pharmaceutically acceptable carrier. Specifically, the pharmaceutical composition of the present invention can be prepared by ordinary formulation techniques as a tablet, pill, capsule, granule, powder, dispersion, liquid, emulsion, suspension, injection or the like, by adding common diluents, fillers, binders, disintegrants, coatings, sugar coatings, pH adjusting agents, dissolving agents, or aqueous or non-aqueous solvents.

The present invention will now be described based on the following specific examples. However, the present invention is not limited to these examples.

REFERENCE EXAMPLE 1

(2R,5R)-2-allyl-2-(4-bromo-2-chlorophenyl)ethyl-3,6-dimethoxy-5-isopropyl-2,5-dihydropyrazine

[Chemical formula 43]

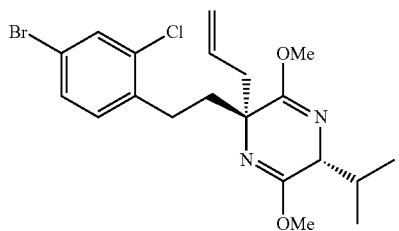

Under an argon atmosphere, an n-butyllithium-hexane solution (1.60 mol/L, 11.16 mL) was added at −78° C. to a solution of (5R)-2-allyl-3,6-dimethoxy-5-isopropyl-2,5-dihydropyrazine (3.64 g) in tetrahydrofuran (60 mL) to form a reaction solution. This reaction solution was then stirred at −78° C. for 30 minutes. A solution of 4-bromo-2-chloro-1-(2-iodoethyl)benzene (6.73 g) in tetrahydrofuran (20 mL) was added to the reaction solution, and the reaction solution was stirred at −78° C. for 30 minutes and then at 0° C. for 1 hour. Water was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=70:1) to obtain the target product (6.04 g) as a colorless oil.

$^1$H NMR (CDCl$_3$, 400 MHz): δ 0.69 (3H, d, J=6.7 Hz), 1.10 (3H, d, J=6.7 Hz), 1.79 (1H, ddd, J=12.8, 11.6, 4.9 Hz), 2.02 (1H, ddd, J=12.8, 11.6, 4.9 Hz), 2.27-2.48 (4H, m), 2.54 (1H, dd, J=13.4, 7.3 Hz), 3.69 (3H, s), 3.70 (3H, s), 3.95 (1H, d, J=3.1 Hz), 4.97 (1H, dd, 10.4, 2.4 Hz), 5.01 (1H, d, J=17.7 Hz), 5.61-5.72 (1H, m), 7.01 (1H, d, J=7.9 Hz), 7.27 (1H, dd, J=7.9, 1.8 Hz), 7.47 (1H, d, J=1.8 Hz).

ESIMS (+): 441 [M+H]$^+$.

REFERENCE EXAMPLE 2

Methyl (R)-2-allyl-4-(4-bromo-2-chlorophenyl)-2-t-butoxycarbonylamino butyrate

[Chemical formula 44]

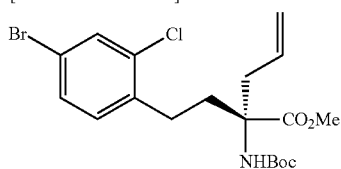

A solution of 50% trifluoroacetic acid—water (108 mL) was added to the compound of Reference Example 1 (5.44 g) to form a first reaction solution. This first reaction solution was stirred at normal temperature for 1 hour, and then left to stand at normal temperature overnight. The first reaction solution was neutralized with a saturated sodium bicarbonate aqueous solution, and extracted with ethyl acetate. The extract was washed with water and saturated brine, and then dried over anhydrous sodium sulfate. The extract was concentrated, and then the resultant residue was dissolved in acetonitrile (86 mL). Then, di-tert-butoxydicarbonate (11.0 g) was added to form a second reaction solution. The second reaction solution was stirred at normal temperature for 1 hour and then left to stand at normal temperature overnight. Next, water was added to the second reaction solution, and the second reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=6:1) to obtain the target product (6.16 g) as a colorless oil.

$^1$H NMR (CDCl$_3$, 400 MHz): δ 1.45 (9H, s), 2.08 (1H, ddd, J=13.4, 11.0, 5.5 Hz), 2.39-2.51 (2H, m), 2.51-2.61 (1H, m), 2.67 (1H, td, J=12.8, 4.9 Hz), 3.00-3.14 (1H, m), 3.74 (3H, s), 5.07 (1H, d, J=4.9 Hz), 5.10 (1H, s), 5.52-5.69 (1H, m), 7.03 (1H, d, J=7.9 Hz), 7.29 (1H, dd, J=7.9, 1.8 Hz), 7.48 (1H, d, J=1.8 Hz).

ESIMS (+): 446 [M+H]$^+$.

REFERENCE EXAMPLE 3

(R)-2-[2-(4-bromo-2-chlorophenyl)ethyl]-2-t-butoxycarbonylamino-4-penten-1-ol

[Chemical formula 45]

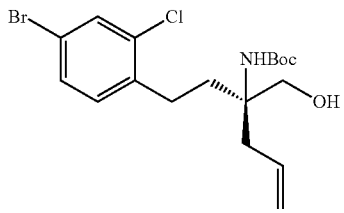

Lithium borohydride (1.04 g) was added under ice cooling to a solution of the compound of Reference Example 2 (6.16 g) in tetrahydrofuran (95 mL) to form a reaction solution. Next, ethanol (9.5 mL) was added dropwise to the reaction solution. The resultant solution was then stirred for 2 hours under ice cooling. A 10% citric acid aqueous solution was added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant product was purified by silica gel column chromatography (hexane:ethyl acetate=2:1) to obtain the target product (3.20 g) as a colorless solid.

$^1$H NMR (CDCl$_3$, 400 MHz): δ 1.43 (9H, s), 1.80-1.94 (2H, m), 2.32 (1H, td, J=14.1, 7.9 Hz), 2.44 (1H, dd, J=14.1, 6.7 Hz), 2.63-2.77 (2H, m), 3.69-3.79 (2H, m), 4.09 (1H, br s), 4.72 (1H, s), 5.19 (1H, dd, J=6.1, 1.8 Hz), 5.22 (1H, s), 5.80-5.91 (1H, s), 7.11 (1H, d, J=7.9 Hz), 7.31 (1H, dd, J=7.9, 1.8 Hz), 7.49 (1H, d, J=1.8 Hz).

ESIMS (+): 418 [M+H]$^+$.

REFERENCE EXAMPLE 4

(2R,5R)-2-(4-bromo-2-chlorophenyl)ethyl-3,6-dimethoxy-5-isopropyl-2-propyl-2,5-dihydropyrazine

[Chemical formula 46]

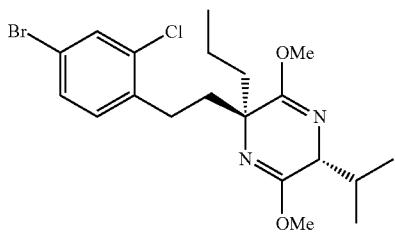

The target product (8.01 g) was obtained as a colorless oil by reacting (5R)-3,6-dimethoxy-2-propyl-5-isopropyl-2,5-dihydropyrazine (5.21 g) in the same manner as in Reference Example 1.

$^1$H NMR (CDCl$_3$, 400 MHz): δ 0.70 (3H, d, J=6.7 Hz), 0.86 (3H, t, J=7.3 Hz), 1.11 (3H, d, J=6.7 Hz), 1.15-1.30 (2H, m), 1.49-1.62 (1H, m), 1.71-1.84 (2H, m), 1.98 (1H, td, J=12.4, 4.8 Hz), 2.29-2.47 (3H, m), 3.69 (3H, s), 3.70 (3H, s), 3.95 (1H, d, J=3.0 Hz), 7.01 (1H, d, J=7.9 Hz), 7.27 (1H, dd, J=7.9, 1.8 Hz), 7.46 (1H, d, J=1.8 Hz).

ESIMS (+): 443 [M+H]$^+$.

REFERENCE EXAMPLE 5

Methyl (S)-4-(4-bromo-2-chlorophenyl)-2-t-butoxycarbonylamino-2-propylbutyrate

[Chemical formula 47]

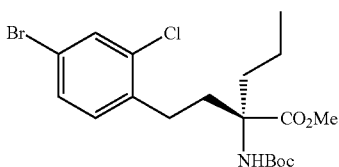

The target product (35.6 g) was obtained as a colorless oil by reacting the compound of Reference Example 4 (53.4 g) in the same manner as in Reference Example 2.

$^1$H NMR (CDCl$_3$, 400 MHz): δ 0.89 (3H, t, J=7.3 Hz). 0.96-1.10 (1H, m), 1.25-1.39 (1H, m), 1.46 (9H, s), 1.69 (1H, ddd, J=13.9, 11.5. 4.8 Hz), 1.99-2.10 (1H, m), 2.20-2.35 (1H, m), 2.42 (1H, ddd, J=13.9, 11.5, 4.8 Hz), 2.49-2.60 (1H, m), 2.64 (1H, td, J=13.9, 4.8 Hz), 3.74 (3H, s), 5.62 (1H, br s), 7.03 (1H, d, J=8.5 Hz), 7.29 (1H, dd, J=8.5, 1.8 Hz), 7.48 (1H, J=1.8 Hz).

ESIMS (+): 448 [M+H]$^+$.

REFERENCE EXAMPLE 6

(R)-2-[2-(4-bromo-2-chlorophenyl)ethyl]-2-t-butoxycarbonylaminopentan-1-ol

[Chemical formula 48]

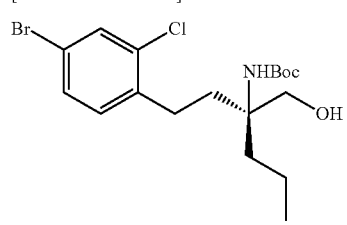

The target product (28.6 g) was obtained as a colorless solid by reacting the compound of Reference Example 5 (35.6 g) in the same manner as in Reference Example 3.

$^1$H NMR (CDCl$_3$, 400 MHz): δ 0.96 (3H, t, J=7.3 Hz), 1.29-1.42 (2H, m), 1.44 (9H, s), 1.53-1.62 (2H, m), 1.81 (1H, ddd, J=13.9, 11.5, 5.4 Hz), 1.93 (1H, ddd, J=13.9, 11.5, 5.4 Hz), 2.59-2.75 (2H, m), 3.73 (2H, d, J=6.7 Hz), 4.15 (1H, br s), 4.62 (1H, br s), 7.11 (1H, d, J=7.9 Hz), 7.31 (1H, dd, J=7.9, 1.8 Hz), 7.49 (1H, d, J=1.8 Hz).

ESIMS (+): 420 [M+H]$^+$.

REFERENCE EXAMPLE 7

1-Cyclopropyl-4-(methoxymethoxy)benzene

[Chemical formula 49]

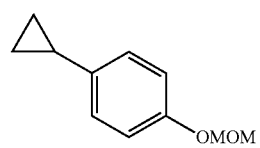

Diisopropylethylamine (77.6 mL) and chloromethyl methyl ether (33.7 mL) were added to a solution of 4-cyclopropylphenol (24.0 g) in methylene chloride (250 mL) to form a reaction solution. This reaction solution was stirred for 15 minutes under ice cooling, and then left overnight at normal temperature. Water was added to the reaction solution, and the reaction solution was extracted with ethyl acetate. The extract was washed with a 1 mol/L sodium hydroxide aqueous solution, water and saturated brine in that order, and then dried over anhydrous sodium sulfate. The anhydrous sodium sulfate was removed by filtration, and then the solvent was removed by distillation under reduced pressure to obtain the target product (27.6 g) as a colorless oil.

$^1$H NMR (CDCl$_3$, 400 MHz): δ 0.59-0.62 (2H, m), 0.86-0.93 (2H, m), 1.80-1.90 (1H, m), 3.47 (3H, s), 5.14 (2H, s), 6.94 (2H, dt, J=9.2, 2.4 Hz), 7.01 (2H, dt, J=9.2, 2.4 Hz).

EIMS (+): 178 [M]$^+$.

REFERENCE EXAMPLE 8

5-Cyclopropyl-2-(methoxymethoxy)-benzenethiol

[Chemical formula 50]

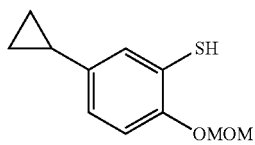

Under an argon atmosphere, an n-butyllithium-hexane solution (1.59 mol/L, 63.5 mL) was added under ice cooling to a solution of the compound of Reference Example 7 (15.0 g) in tetrahydrofuran (120 mL) to form a reaction solution. This reaction solution was stirred for 1 hour at the same temperature. The reaction solution was cooled to −78° C. Sulfur (3.23 g) was added, and the solution was stirred for 30 minutes and then for 10 minutes under ice cooling. A saturated ammonium chloride aqueous solution was added to the reaction solution. The solution was extracted with diethyl ether, and then the organic layer was extracted with a 1 mol/L sodium hydroxide aqueous solution. The pH of the solution was lowered to 4 using concentrated hydrochloric acid, and then the solution was extracted with diethyl ether. The organic layer was washed with saturated brine, and then dried over anhydrous sodium sulfate. The anhydrous sodium sulfate was removed by filtration, and then the solvent was removed by distillation under reduced pressure to obtain the target product (12.1 g) as a colorless oil.

$^1$H NMR (CDCl$_3$, 400 MHz): δ 0.61 (2H, dt, J=6.1, 4.9 Hz), 0.86-0.92 (2H, m), 1.75-1.86 (1H, m), 3.50 (3H, s), 3.76 (1H, s), 5.20 (2H, s), 6.80 (1H, dd, J=8.6, 2.4 Hz), 6.98 (1H, d, J=8.6 Hz), 6.98 (1H, d, J=2.4 Hz).

EIMS (+): 210 [M]$^+$.

REFERENCE EXAMPLE 9

6-Ethoxy-1,3-benzoxathiol-2-one

[Chemical formula 51]

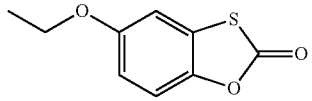

Potassium carbonate (533 mg) and ethyl iodide (160 μL) were added to a solution of 6-hydroxy-1,3-benzoxathiol-2-one (336 mg) in N,N-dimethylformamide (10 mL) to form a reaction solution. This reaction solution was stirred for 4 hours at normal temperature. Water was added to the reaction solution. The precipitated crystals were filtered off, thoroughly washed with water and diisopropyl ether, and then dried under reduced pressure to obtain the target product (245 mg) as a colorless solid.

$^1$H NMR (CDCl$_3$, 400 MHz): δ 1.42 (3H, t, J=6.7 Hz). 4.02 (2H, q, J=6.7 Hz), 6.84 (1H, dd, J=8.6, 2.4 Hz), 6.91 (1H, d, J=2.4 Hz), 7.18 (1H, d, J=8.6 Hz).

EIMS (+): 196 [M]$^+$.

REFERENCE EXAMPLE 10

5-Ethoxy-2-hydroxybenzenethiol

[Chemical formula 52]

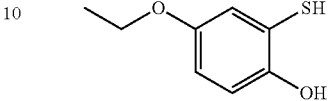

Under an argon atmosphere, lithium aluminum hydride (119 mg) was added under ice cooling to a solution of the compound of Reference Example 9 (245 mg) in tetrahydrofuran (12.5 mL) to form a reaction solution. This reaction solution was stirred for 30 minutes under ice cooling. Then, 1 mol/L hydrochloric acid was added to the reaction solution, and the reaction solution was extracted with ethyl acetate. The extract was washed with water and saturated brine in that order, and then dried over anhydrous sodium sulfate. The anhydrous sodium sulfate was removed by filtration, and the solvent was removed by distillation under reduced pressure to obtain the target product (210 mg) as a colorless oil.

$^1$H NMR (CDCl$_3$, 400 MHz): δ 1.38 (3H, t, J=7.3 Hz). 3.10 (1H, s), 3.96 (2H, q, J=7.3 Hz), 5.73 (1H, s), 6.78 (1H, dd, J=9.2, 3.1 Hz), 6.87 (1H, d, J=9.2 Hz), 6.98 (1H, d, J=3.1 Hz).

SIMS (+): 170 [M]$^+$.

REFERENCE EXAMPLE 11

6-t-Butyldimethylsilyloxy-1,3-benzoxathiol-2-one

[Chemical formula 53]

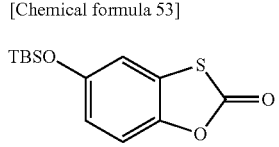

Imidazole (972 mg) and t-butylchlorodimethylsilane (2.15 g) were added to a solution of 6-hydroxy-1,3-benzoxathiol-2-one (2.00 g) in N,N-dimethylformamide (60 mL) to form a reaction solution. This reaction solution was stirred for 4 hours at normal temperature. Water was then added to the reaction solution, and the reaction solution was extracted with ethyl acetate. The extract was washed with water and saturated brine in that order, and then dried over anhydrous sodium sulfate. The anhydrous sodium sulfate was removed by filtration, and then the solvent was removed by distillation under reduced pressure. The resultant residue was then purified by silica gel column chromatography (hexane:ethyl acetate=20:1) to obtain the target product (3.00 g) as a colorless oil.

$^1$H NMR (CDCl$_3$, 400 MHz): δ 0.20 (6H, s), 0.98 (9H, s), 6.77 (1H, dd, J=8.6, 2.4 Hz), 6.87 (1H, d, J=2.4 Hz), 7.14 (1H, d, J=8.6 Hz).

CIMS (+): 283 [M+H]$^+$.

REFERENCE EXAMPLE 12

5-t-Butyldimethylsilyloxy-2-hydroxybenzenethiol

[Chemical formula 54]

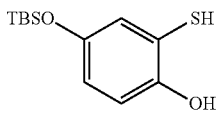

The target product (2.72 g) was obtained as a colorless oil by reacting the compound of Reference Example 11 (3.00 g) in the same manner as in Reference Example 10.
$^1$H NMR (CDCl$_3$, 400 MHz): δ 0.16 (6H, s), 0.97 (9H, s), 3.06 (1H, s), 5.73 (1H, s), 6.71 (1H, dd, J=8.6, 2.4 Hz), 6.81 (1H, d, J=2.4 Hz), 6.93 (1H, d, J=8.6 Hz).
CIMS (+): 257 [M+H]$^+$.

REFERENCE EXAMPLE 13

(R)-2-allyl-2-t-butoxycarbonylamino-4-{2-chloro-4-(5-ethoxy-2-hydroxyphenylthio)phenyl}butan-1-ol

[Chemical formula 55]

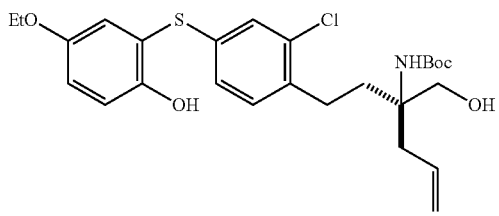

Under an argon gas atmosphere, a solution of tris(dibenzylideneacetone)dipalladium (87.0 mg) and 4,5-bis(diphenylphosphino)-9,9-dimethylxanthene (111 mg) in dioxane (1.8 mL) as a reaction solution was heated to reflux for 30 minutes. Next, a solution of the compound of Reference Example 3 (400 mg) in dioxane (2.0 mL), diisopropylethylamine (0.32 mL), and a solution of the compound of Reference Example 10 (195 mg) in dioxane (1.0 mL) was added to the reaction solution, and the reaction solution was stirred for 3 hours while heating to reflux. The compound of Reference Example 10 (33.0 mg) was further added to the reaction solution, which was then heated to reflux for 14 hours. Then, water was added under ice cooling. Insoluble matter was removed by filtration using Celite, And the filtrate was washed with ethyl acetate. The filtrate was extracted with ethyl acetate. The organic layer was successively washed with water and saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=10:1) to obtain the target product (342 mg) as a brown oil.
$^1$H NMR (CDCl$_3$, 400 MHz): δ 1.39 (3H, t, J=6.7 Hz), 1.43 (9H, s), 1.77-1.91 (2H, m), 2.32 (1H, dd, J=13.9, 7.9 Hz), 2.43 (1H, dd, J=13.9, 7.3 Hz), 2.59-2.75 (2H, m), 3.67-3.79 (2H, m), 3.97 (2H, q, J=6.7 Hz), 4.15 (1H, brs), 4.71 (1H, s), 5.17 (1H, d, J=3.6 Hz), 5.21 (1H, s), 5.78-5.91 (1H, m), 6.04 (1H, s), 6.91 (1H, dd, J=7.9, 1.8 Hz), 6.93-7.21 (1H, m).
ESIMS (+): 508 [M+H]$^+$.

REFERENCE EXAMPLE 14

(R)-2-allyl-2-t-butoxycarbonylamino-4-{2-chloro-4-(2-t-butoxycarbonylhydroxy-5-ethoxyphenylthio)phenyl}butan-1-ol

[Chemical formula 56]

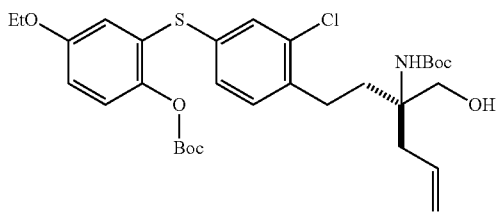

Under an argon atmosphere, di-tert-butyldicarbonate (101 mg) and triethylamine (0.052 mL) were added to a solution of the compound of Reference Example 13 (156 mg) in acetonitrile (3.1 mL) to form a reaction solution. This reaction solution was stirred for 2.5 days at normal temperature. Water was added to the reaction solution, and the reaction solution was extracted with ethyl acetate. The organic layer was successively washed with water and saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=10:1) to obtain the target product (182 mg) as a colorless oil.
$^1$H NMR (CDCl$_3$, 400 MHz): δ 1.36 (3H, t, J=7.3 Hz), 1.44 (9H, s), 1.51 (9H, s), 1.87 (2H, ddd, J=11.5, 6.1, 1.8 Hz), 2.33 (1H, dd, J=13.9, 8.5 Hz), 2.45 (1H, dd, J=13.9, 6.7 Hz), 2.64-2.78 (2H, m), 3.68-3.81 (2H, m), 3.94 (2H, q, J=7.3 Hz), 4.73 (1H, s), 5.19 (1H, d, J=3.6 Hz), 5.22 (1H, s), 5.79-5.93 (1H, m), 6.78-6.84 (2H, m), 7.09 (1H, d, J=8.5 Hz), 7.15 (2H, s), 7.33 (1H, s).
ESIMS (+): 608 [M+H]$^+$.

REFERENCE EXAMPLE 15

(R)-2-allyl-2-t-butoxycarbonylamino-4-{2-chloro-4-(2-t-butoxycarbonylhydroxy-5-ethoxyphenylthio)phenyl}-1-dimethoxyphosphoryloxybutane

[Chemical formula 57]

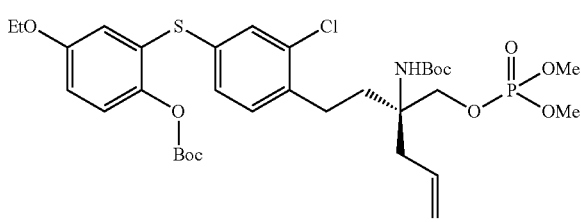

Under an argon gas atmosphere, carbon tetrabromide (190 mg) and trimethyl phosphite (0.068 mL) were added under ice cooling to a solution of the compound of Reference Example 14 (175 mg) in pyridine (0.57 mL) to form a reaction solution. This reaction solution was stirred for 4 hours at the same temperature. Water was added to the reaction solution, and the reaction solution was extracted with ethyl acetate. The organic layer was successively washed with 1 mol/L hydrochloric acid, water, and saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=3:1) to obtain the target product (194 mg) as a colorless oil.

$^1$H NMR (CDCl$_3$, 400 MHz): δ 1.36 (3H, t, J=7.3 Hz), 1.44 (9H, s), 1.51 (9H, s), 1.75-1.92 (1H, m), 1.90-2.10 (1H, m), 2.42-2.57 (2H, m), 2.64-2.75 (2H, m), 3.77 (3H, s), 3.80 (3H, d, J=1.2), 3.90-4.01 (2H, m), 4.11 (1H, dd, J=9.7, 4.8 Hz), 4.22 (1H, dd, J=9.7, 4.8 Hz), 4.60 (1H, brs), 5.17-5.25 (2H, m), 5.75-5.88 (1H, m), 6.78-6.84 (2H, m), 7.09 (1H, d, J=8.5 Hz), 7.10-7.17 (2H, m), 7.32 (1H, t, J=1.8 Hz).

ESIMS (+): 716 [M+H]$^+$.

EXAMPLE 1

(R)-2-allyl-2-amino-4-{2-chloro-4-(5-ethoxy-2-hydroxyphenylthio)phenyl}butylphosphoric acid monoester

[Chemical formula 58]

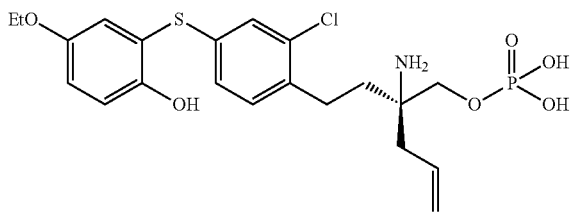

A hydrogen chloride-methanol solution (5-10%, 15 mL) was added to the compound of Reference Example 15 (193 mg) to form a first reaction solution. This first reaction solution was stirred for 1 day at normal temperature. The solvent was removed by distillation under reduced pressure, and then, under an argon atmosphere, acetonitrile (2.7 mL) was added to the residue to form a second reaction solution. Iodotrimethylsilane (0.19 mL) was added to this second reaction solution under ice cooling. Next, the second reaction solution was stirred for 2 hours at the same temperature. Cold water in large excess was added to the second reaction solution. The supernatant was removed, and then the obtained brown oil was dissolved in methanol. The solvent was removed by distillation under reduced pressure, and then the resultant product was dissolved in tetrahydrofuran, and acetonitrile was added to the resultant solution. The resulting precipitate was collected by filtration to obtain the target product (63.3 mg) as a colorless solid.

Optical rotation: [α]$_D^{26}$+2.74 (c 0.31, MeOH).

$^1$H NMR (DMSO-d$_6$, 400 MHz): δ 1.23 (1H, t, J=6.7 Hz), 1.60-1.77 (1H, m), 2.30-2.50 (1H, m), 2.62-2.73 (1H, m), 3.77 (2H, dt, J=22.4, 12.1 Hz), 3.87 (2H, q, J=6.7 Hz), 5.16-5.29 (2H, m), 5.77-5.84 (1H, m), 6.71 (1H, d, J=2.4 Hz), 6.79-6.87 (2H, m), 7.07-7.14 (2H, m), 7.26 (1H, d, J=7.9 Hz).

HRESIMS (+): 488.10694 (Calcd. for C$_{21}$H$_{28}$ClNO$_6$PS 488.10635).

REFERENCE EXAMPLE 16

(R)-2-allyl-2-t-butoxycarbonylamino-4-{2-chloro-4-(5-cyclopropyl-2-methoxymethyloxyphenylthio)phenyl}butan-1-ol

[Chemical formula 59]

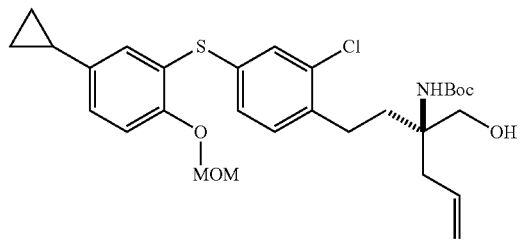

The target product (2.2 g, including impurities) was obtained as a green oil by reacting the compound of Reference Example 3 (1.5 g) and the compound of Reference Example 8 (1.13 g) in the same manner as in Reference Example 13. The materials were used in the next reaction as is without any further purification.

REFERENCE EXAMPLE 17

(R)-2-allyl-2-t-butoxycarbonylamino-4-{2-chloro-4-(5-cyclopropyl-2-methoxymethyloxyphenylthio)phenyl}-1-dimethoxyphosphoryloxybutane

[Chemical formula 60]

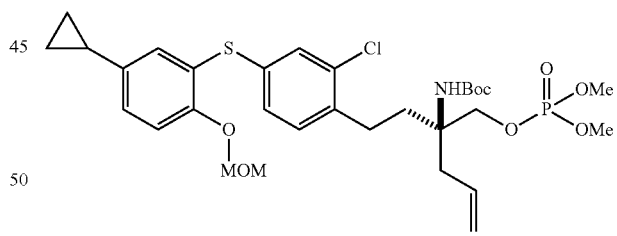

The target product (1.43 g) was obtained as a brown oil by reacting the compound of Reference Example 16 (2.2 g, including impurities) in the same manner as in Reference Example 15.

$^1$H NMR (CDCl$_3$, 400 MHz): δ 0.57-0.60 (2H, m), 0.88-0.91 (2H, m), 1.44 (9H, s), 1.78-1.84 (2H, m), 1.96-2.04 (1H, m), 2.44-2.56 (2H, m), 2.68-2.73 (2H, m), 3.38 (3H, s), 3.77 (3H, s), 3.80 (3H, s), 4.12 (1H, dd, J=9.8, 4.3 Hz), 4.23 (1H, dd, J=9.8, 4.3 Hz), 4.59 (1H, brs), 5.15 (2H, s), 5.19-5.23 (2H, m), 5.76-5.85 (1H, m), 6.98 (1H, d, J=8.6, 1.8 Hz), 7.00 (1H, d, J=1.8 Hz), 7.08 (1H, d, J=7.3 Hz), 7.09 (1H, d, J=7.3 Hz), 7.17 (1H, d, J=8.6 Hz), 7.23 (1H, d, J=1.2 Hz).

ESIMS (+): 656 [M+H]$^+$.

REFERENCE EXAMPLE 18

(R)-2-t-butoxycarbonylamino-4-{2-chloro-4-(5-cyclopropyl-2-methoxymethyloxyphenylthio)phenyl}-1-dimethoxyphosphoryloxy-2-(1-hydroxypropyl)butane

[Chemical formula 61]

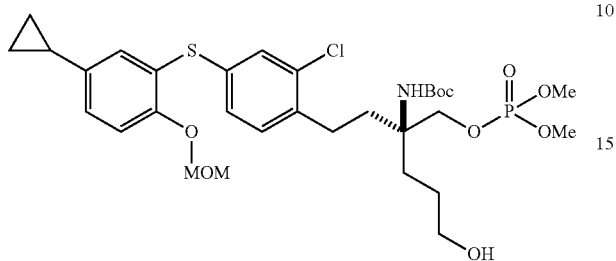

Under an argon gas atmosphere, the compound of Reference Example 17 (1.41 g) was dissolved in tetrahydrofuran (20 mL). A borane-tetrahydrofuran complex (1.01 mol/L tetrahydrofuran solution, 3.2 mL) was then added dropwise to the solution of the compound of Reference Example 17 under ice cooling to form a reaction solution. This reaction solution was stirred at the same temperature for 1.5 hours. Then, water (20 mL) and sodium perborate hydrate (644 mg) were added under ice cooling, and the reaction solution was stirred for 3 hours at normal temperature. The reaction solution was diluted with water, and then extracted with ethyl acetate. The organic layer was washed with saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=1:2) to obtain the target product (979 mg) as a colorless oil.

$^1$H NMR (CDCl$_3$, 400 MHz): δ 0.56-0.60 (2H, m), 0.87-0.92 (2H, m), 1.40 (9H, s), 1.60-1.66 (2H, m), 1.75-1.82 (4H, m), 2.68 (2H, t, J=8.6 Hz), 3.38 (3H, s), 3.66-3.69 (2H, m), 3.78 (3H, d, J=3.7 Hz), 3.80 (3H, d, J=3.7 Hz), 4.12-4.16 (1H, m), 4.22-4.26 (1H, m), 4.61 (1H, brs), 5.15 (2H, s), 6.97 (1H, dd, J=8.6, 2.5 Hz), 6.98 (1H, d, J=8.6, 1.8 Hz), 7.00 (1H, d, J=1.8 Hz), 7.06 (1H, d, J=7.3 Hz), 7.09-7.12 (2H, m), 7.23 (1H, d, J=1.8 Hz).

ESIMS (+): 674 [M+H]$^+$.

REFERENCE EXAMPLE 19

(R)-2-amino-4-{2-chloro-4-(5-cyclopropyl-2-hydroxyphenylthio)phenyl}-2-(1-hydroxypropyl)butylphosphoric acid monoester

[Chemical formula 62]

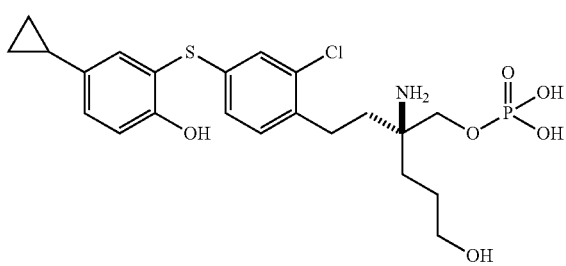

The target product (120 mg) was obtained as a colorless amorphous substance by reacting the compound of Reference Example 18 (535 mg) in the same manner as in Example 1.

$^1$H NMR (DMSO-d$_6$, 400 MHz): δ 0.49-0.53 (2H, m), 0.80-0.84 (2H, m), 1.46-1.81 (7H, m), 2.61 (2H, brs), 3.33-3.39 (2H, m), 3.71 (2H, brs), 6.85 (1H, d, J=8.6 Hz), 6.92-6.99 (4H, m), 7.25 (1H, d, J=7.3 Hz).

HRESIMS (+): 502.12175 (Calcd. for C$_{22}$H$_{30}$ClNO$_6$PS 502.12200).

REFERENCE EXAMPLE 20

(S)-2-t-butoxycarbonylamino-4-{2-chloro-4-(2-t-butoxycarbonyloxy-5-ethoxyphenylthio)phenyl}-2-propylbutan-1-ol

[Chemical formula 63]

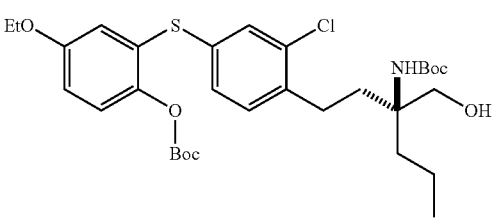

The compound of Reference Example 14 (122 mg) was dissolved in ethanol (2 mL), and then 10% palladium on activated carbon (12 mg) was added to the solution of the compound of Reference Example 14 to form a reaction solution. This reaction solution was stirred for 10 hours at normal temperature under a hydrogen atmosphere (1 atm). Insoluble matter was removed using Celite. The solvent in the filtrate was removed by distillation under reduced pressure to obtain the target product (123 mg) as a colorless oil.

$^1$H NMR (CDCl$_3$, 400 MHz): δ 0.96 (3H, t, J=7.3 Hz), 1.36 (3H, t, J=7.3 Hz), 1.39-1.58 (4H, m), 1.51 (9H, s), 1.59 (9H, s), 1.53-1.60 (2H, m), 1.75-1.84 (1H, m), 1.86-1.95 (1H, m), 2.60-2.74 (2H, m), 3.74 (2H, d, J=6.1 Hz), 3.94 (2H, q, J=7.3 Hz), 4.22 (1H, brs), 4.64 (1H, brs), 6.78-6.83 (2H, m), 7.09 (1H, d, J=8.6 Hz), 7.15-7.16 (1H, m), 7.33 (1H, d, J=1.2 Hz).

ESIMS (+): 610 [M+H]$^+$.

REFERENCE EXAMPLE 21

(S)-2-t-butoxycarbonylamino-4-{2-chloro-4-(2-t-butoxycarbonyloxy-5-ethoxyphenylthio)phenyl}-1-dimethoxyphosphoryloxy-2-propylbutane

[Chemical formula 64]

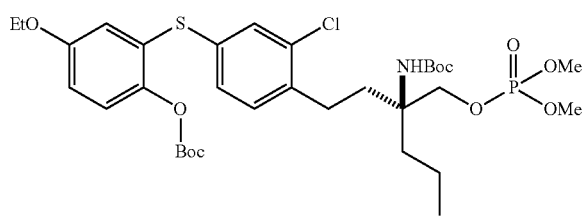

The target product (106 mg) was obtained as a colorless oil by reacting the compound of Reference Example 20 (100 mg) in the same manner as in Reference Example 15.

$^1$H NMR (CDCl$_3$, 400 MHz): δ 0.95 (3H, t, J=7.3 Hz), 1.47 (9H, s), 1.51 (9H, s), 1.63-1.82 (5H, m), 1.99-2.05 (1H, m), 2.64-2.69 (2H, m), 3.77 (3H, d, J=1.2 Hz), 3.94 (2H, q, J=7.3 Hz), 4.09-4.12 (1H, m), 4.23-4.26 (1H, m), 4.51 (1H, brs), 6.79-6.83 (2H, m), 7.09 (1H, d, J=8.6 Hz), 7.12 (1H, d, J=7.9 Hz), 7.15 (1H, dd, J=7.9, 1.8 Hz), 7.33 (1H, d, J=1.8 Hz).
ESIMS (+): 718 [M+H]$^+$.

EXAMPLE 2

(S)-2-amino-4-{2-chloro-4-(5-ethoxy-2-hydroxyphenylthio)phenyl}-2-propylbutylphosphoric acid monoester

[Chemical formula 65]

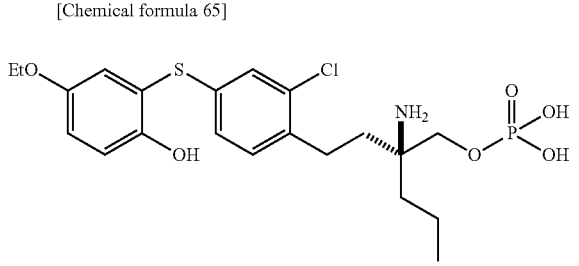

The target product (37 mg) was obtained as a colorless solid by reacting the compound of Reference Example 21 (103 mg) in the same manner as Example 1.
Optical rotation: [α]$_D^{28}$ −5.7 (c 0.34, MeOH).
Optical rotation: [α]$_D^{25}$ +16.2 (c 0.5, DMF).
$^1$H NMR (DMSO-d$_6$, 400 MHz): δ 0.89 (3H, t, J=7.3 Hz), 1.23 (3H, t, J=7.3 Hz), 1.29-1.32 (2H, m), 1.50-1.75 (4H, m), 2.61-2.66 (2H, m), 3.70-3.81 (2H, m), 3.87 (2H, q, J=7.3 Hz), 6.71 (1H, d, J=3.1 Hz), 6.82 (1H, dd, J=8.6, 3.1 Hz), 6.86 (1H, d, J=8.6 Hz), 7.10 (1H, dd, J=8.0, 1.8 Hz), 7.12 (1H, d, J=1.8 Hz), 7.28 (1H, d, J=8.0 Hz).
HRESIMS (+): 490.12195 (Calcd. for C$_{21}$H$_{30}$ClNO$_6$PS 490.12200).

REFERENCE EXAMPLE 22

(R)-2-allyl-2-t-butoxycarbonylamino-4-{2-chloro-4-(5-t-butyldimethylsilyloxy-2-hydroxyphenylthio)phenyl}butan-1-ol

[Chemical formula 66]

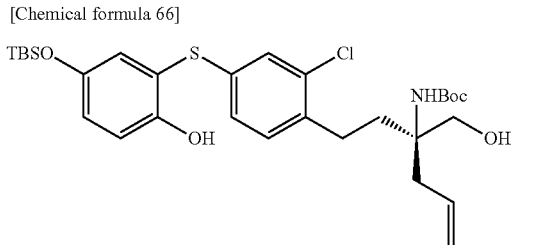 [SMILES: C=CC[C@@](CO)(CCc1ccc(Sc2cc(O[Si](C)(C)C(C)(C)C)ccc2O)cc1Cl)NC(=O)OC(C)(C)C]

The target product (3.22 g) was obtained as a brown oil by reacting the compound of Reference Example 3 (3.6 g) and the compound of Reference Example 12 (2.65 g) in the same manner as in Reference Example 13.
$^1$H NMR (CDCl$_3$, 400 MHz): δ 0.17 (6H, s), 0.97 (9H, s), 1.58 (9H, s), 1.81-1.88 (2H, m), 2.32 (1H, dd, J=13.5, 8.0 Hz), 2.43 (1H, dd, J=13.5, 6.7 Hz), 2.62-2.70 (1H, m), 3.68-3.78 (2H, m), 4.71 (1H, brs), 5.17-5.21 (2H, m), 5.80-5.90 (1H, m), 6.05 (1H, s), 6.87-6.98 (4H, m), 7.03 (1H, d, J=1.8 Hz), 7.10 (1H, d, J=8.0 Hz).
ESIMS (+): 594 [M+H]$^+$.

REFERENCE EXAMPLE 23

(R)-2-allyl-2-t-butoxycarbonylamino-4-{2-chloro-4-(5-t-butyldimethylsilyloxy-2-methoxymethyloxyphenylthio)phenyl}butan-1-ol

[Chemical formula 67]

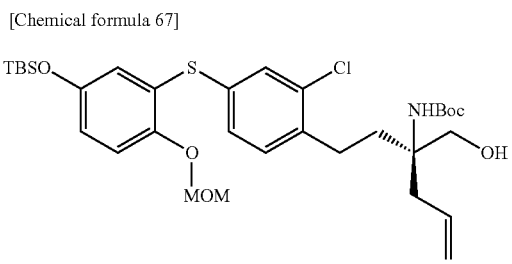

Potassium carbonate (446 mg) was added to a solution of the compound of Reference Example 22 (1.75 g) in acetone (14.7 mL). Then, chloromethyl methyl ether (0.25 mL) was added dropwise under ice cooling to form a reaction solution. The reaction solution was then stirred for 4 hours at the same temperature. A 10% citric acid aqueous solution was added to the reaction solution, and the reaction solution was extracted with ethyl acetate. The combined organic layers were washed with saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=4:1) to obtain the target product (1.44 g) as a colorless oil.
$^1$H NMR (CDCl$_3$, 400 MHz): δ 0.08 (6H, s), 0.91 (9H, s), 1.44 (9H, s), 1.78-1.95 (2H, m), 2.34 (1H, dd, J=14.1, 7.9 Hz), 2.46 (1H, dd, J=14.1, 6.7 Hz), 2.65-2.82 (1H, m), 3.45 (3H, s), 3.68-3.82 (2H, m), 4.74 (1H, brs), 5.13 (2H, s), 5.16-5.25 (2H, m), 5.80-5.95 (1H, m), 6.53 (1H, d, J=3.1 Hz), 6.68 (1H, dd, J=9.2, 3.1 Hz), 7.00 (1H, d, J=9.2 Hz), 7.18 (2H, s), 7.32 (1H, s).
ESIMS (+): 638 [M+H]$^+$.

REFERENCE EXAMPLE 24

(R)-2-allyl-2-t-butoxycarbonylamino-4-{2-chloro-4-(5-hydroxy-2-methoxymethyloxyphenylthio)phenyl}butan-1-ol

[Chemical formula 68]

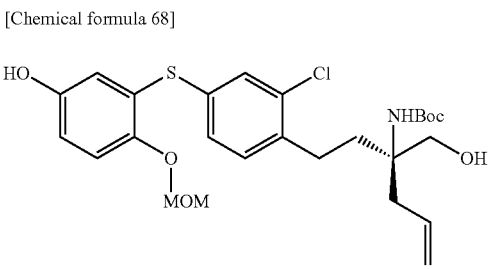

Tetrabutylammonium fluoride (1.0 mol/L tetrahydrofuran solution, 6.20 mL) was added under ice cooling to a solution of the compound of Reference Example 23 (3.96 g) in tetrahydrofuran (31 mL) to form a reaction solution. The reaction solution was then stirred for 1 hour at the same temperature. Water was added to the reaction solution. The tetrahydrofuran was removed from the reaction solution by distillation under reduced pressure, and the resultant residue was extracted with ethyl acetate. The combined organic layers were successively washed with water (20 mL) and saturated brine, and dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=12:1→1:2). The solid obtained by this purification treatment was suspended in hexane-diethyl ether (4:1), and then collected by filtration to obtain the target product (2.87 g) as a colorless solid.

$^1$H NMR (CDCl$_3$, 400 MHz): δ 1.44 (9H, s), 1.80-2.03 (2H, m), 2.34 (1H, dd, J=14.1, 7.9 Hz), 2.40-2.55 (1H, m), 2.70-2.85 (2H, m), 3.47 (3H, s), 3.65-3.78 (2H, m), 4.77 (1H, brs), 5.13 (2H, s), 5.17-5.27 (2H, m), 5.78-5.95 (1H, m), 6.45 (1H, s), 6.65 (1H, dd, J=8.6, 3.1 Hz), 7.00 (1H, d, J=8.6 Hz), 7.21 (2H, s), 7.38 (1H, s).

ESIMS (+): 524 [M+H]$^+$.

REFERENCE EXAMPLE 25

(R)-2-allyl-2-t-butoxycarbonylamino-4-{2-chloro-4-(2-methoxymethyloxy-5-trifluoromethanesulfonyloxyphenylthio)phenyl}butan-1-ol

[Chemical formula 69]

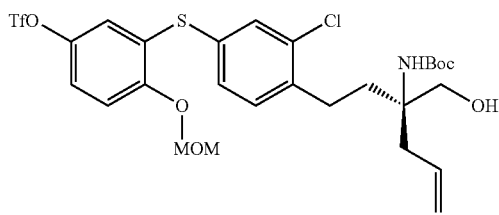

Under an argon gas atmosphere, triethylamine (0.75 mL) and N-phenylbis (trifluoromethanesulfonimide) (954 mg) were added under ice cooling to a suspension of the compound of Reference Example 24 (1.40 g) in dichloromethane (13.4 mL) to form a reaction solution. The reaction solution was then stirred for 3 hours at normal temperature. N-phenylbis (trifluoromethanesulfonimide) (143 mg) was further added to the reaction solution, and the solution was then stirred for 2 hours at normal temperature. Water was added to the reaction solution, and the reaction solution was extracted with ethyl acetate. The combined organic layers were washed with saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=4:1) to obtain the target product (1.77 g) as a colorless solid.

$^1$H NMR (CDCl$_3$, 400 MHz): δ 1.44 (9H, s), 1.83-2.00 (2H, m), 2.34 (1H, dd, J=14.1, 8.6 Hz), 2.47 (1H, dd, J=14.1, 6.7 Hz), 2.70-2.87 (2H, m), 3.47 (3H, s), 3.70-3.85 (2H, m), 4.75 (1H, brs), 5.18-5.26 (2H, m), 5.24 (2H, s), 5.80-5.96 (1H, m), 6.78 (1H, d, J=3.1 Hz), 7.05 (1H, dd, J=9.2, 3.1 Hz), 7.16 (1H, d, J=9.2 Hz), 7.27 (2H, s), 7.43 (1H, d, J=1.2 Hz).

ESIMS (+): 656 [M+H]$^+$.

REFERENCE EXAMPLE 26

(R)-2-allyl-2-t-butoxycarbonylamino-4-{2-chloro-4-(5-cyano-2-m ethoxymethyloxyphenylthio)phenyl}butan-1-ol

[Chemical formula 70]

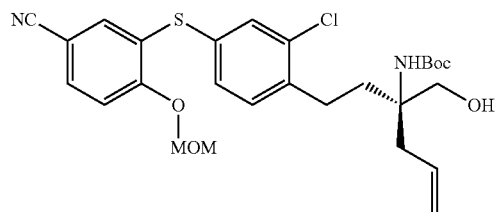

Under an argon gas atmosphere, tetrakistriphenylphosphine palladium (69.3 mg), 1,1'-bis(diphenylphosphino)ferrocene (33.3 mg), and zinc cyanide (141 mg) were added to a solution of the compound of Reference Example 25 (200 mg) in N,N-dimethylformamide (1.5 mL) to form a reaction solution. The reaction solution was then stirred for 4 hours at 80° C. After leaving the reaction solution to cool, water was added thereto. And the reaction solution was extracted with ethyl acetate. The combined organic layers were washed with saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=12:1→1:2) to obtain the target product (114 mg) as a colorless oil.

$^1$H NMR (CDCl$_3$, 400 MHz): δ 1.45 (9H, s), 1.85-2.04 (2H, m), 2.36 (1H, dd, J=13.9, 8.5 Hz), 2.47 (1H, dd, J=13.9, 6.7 Hz), 2.70-2.86 (2H, m), 3.45 (3H, s), 3.70-3.84 (2H, m), 4.76 (1H, brs), 5.17-5.26 (2H, m), 5.29 (2H, s), 5.81-5.97 (1H, m), 7.13-7.21 (2H, m), 7.23-7.32 (2H, m), 7.42 (1H, d, J=1.2 Hz), 7.45 (1H, dd, J=8.5, 1.8 Hz).

ESIMS (+): 533 [M+H]$^+$.

REFERENCE EXAMPLE 27

(R)-2-allyl-2-t-butoxycarbonylamino-4-{2-chloro-4-(5-cyano-2-m ethoxymethyloxyphenylthio)phenyl}-1-dimethoxyphosphoryloxybutane

[Chemical formula 71]

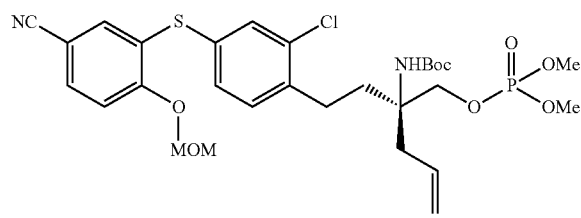

The target product (309 mg) was obtained as a colorless oil by reacting the compound of Reference Example 26 (304 mg) in the same manner as in Reference Example 15.

$^1$H NMR (CDCl$_3$, 400 MHz): δ 1.38 (9H, s), 1.60-1.73 (1H, m), 1.75-1.90 (1H m), 2.35-2.44 (2H, m), 2.62-2.72 (2H, m), 3.25 (3H, s), 3.65 (3H, d, J=1.2 Hz), 3.68 (3H, d, J=1.2 Hz), 3.95-4.05 (1H, m), 4.05-4.18 (1H, m), 5.08-5.20 (2H, m), 5.35 (2H, s), 5.68-5.84 (1H, m), 6.70 (1H, brs), 7.25-7.36 (3H, m), 7.39 (1H, d, J=1.8 Hz), 7.46 (1H, d, J=1.8 Hz), 7.63 (1H, dd, J=8.6, 2.4 Hz).

ESIMS (+): 641 [M+H]$^+$.

REFERENCE EXAMPLE 28

(R)-2-allyl-2-amino-4-{2-chloro-4-(5-cyano-2-hydroxyphenylthio)phenyl}butylphosphoric acid monoester

[Chemical formula 72]

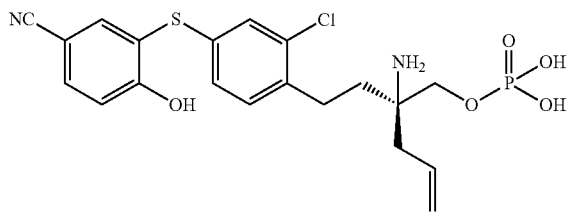

The target product (42.5 mg) was obtained as a colorless solid by reacting the compound of Reference Example 27 (300 mg) in the same manner as in Example 1.

Optical rotation: $[α]_D^{25}$ −9.0 (c 0.50, MeOH).

$^1$H NMR (DMSO-d$_6$, 400 MHz): δ 1.60-1.82 (2H, m), 2.30-2.42 (2H m), 2.62-2.80 (2H, m), 3.68-3.88 (2H, m), 5.14-5.30 (2H, m), 5.72-5.90 (1H, m), 7.06 (1H, d, J=8.5 Hz), 7.14 (1H, dd, J=8.5, 1.8 Hz), 7.26 (1H, d, J=1.8 Hz), 7.31 (1H, d, J=8.5 Hz), 7.50 (1H, d, J=1.8 Hz), 7.62 (1H, dd, J=8.5, 1.8 Hz).

HRESIMS (+): 469.07566 (Calcd. for C$_{20}$H$_{23}$ClN$_2$O$_5$PS 469.07538).

REFERENCE EXAMPLE 29

(S)-2-t-butoxycarbonylamino-4-[2-chloro-4-(5-hydroxy-2-methoxy methyloxyphenylthio)phenyl]-2-propylbutan-1-ol

[Chemical formula 73]

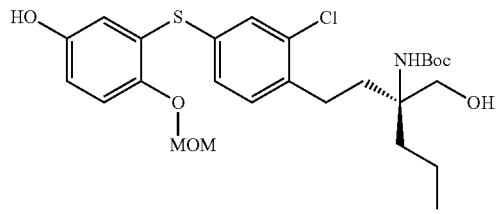

The compound of Reference Example 24 (919 mg) was dissolved in ethanol (17.5 mL), and then 10% palladium on activated carbon (92 mg) was added. The mixture was then stirred for 17.5 hours at normal temperature under a hydrogen atmosphere (1 atm). Solid matter was removed by filtration using Celite. The solvent was removed by distillation under reduced pressure to obtain a residue (916 mg). This residue was dissolved in methanol (20 mL), and then 10% palladium on activated carbon (93 mg) was added. The mixture was then stirred for 5 hours at normal temperature under a hydrogen atmosphere. Additional 10% palladium on activated carbon (92 mg) was added, and the mixture was stirred for further 14.5 hours. Insoluble matter was removed by filtration using Celite, and the solvent was removed by distillation under reduced pressure to obtain the target product (850 mg) as a flesh color solid.

$^1$H NMR (CDCl$_3$, 400 MHz): δ 0.97 (3H, t, J=7.3 Hz), 1.31-1.47 (2H, m), 1.44 (9H, s), 1.49-1.64 (2H, m), 1.83-2.02 (2H, m), 2.63-2.81 (2H, m), 3.48 (3H, s), 3.70 (2H, d, J=6.1 Hz), 4.33 (1H, brs), 4.65 (1H, brs), 4.95 (1H, brs), 5.14 (2H, s), 6.37-6.45 (1H, m), 6.64 (1H, dd, J=8.6, 2.4 Hz), 7.01 (1H, d, J=8.6 Hz), 7.20-7.25 (2H, m), 7.38-7.42 (1H, m).

ESIMS (+): 526 [M+H]$^+$.

REFERENCE EXAMPLE 30

(S)-2-t-butoxycarbonylamino-4-[2-chloro-4-(2-methoxymethyloxy-5-trifluoromethanesulfonyloxyphenylthio)phenyl]-2-propylbutan-1-ol

[Chemical formula 74]

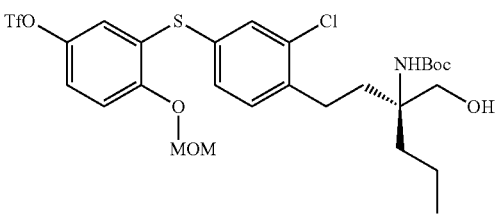

The target product (1.20 g) was obtained as a colorless oil by reacting the compound of Reference Example 29 (1.31 g) in the same manner as in Reference Example 25.

$^1$H NMR (CDCl$_3$, 400 MHz): δ 0.97 (3H, t, J=7.3 Hz), 1.31-1.49 (2H, m), 1.44 (9H, s), 1.56-1.61 (2H, m), 1.80-1.88 (1H, m), 1.91-1.99 (1H, m), 2.67-2.80 (2H, m), 3.47 (3H, s), 3.75 (2H, d, J=5.5 Hz), 4.22 (1H, brs), 4.66 (1H, s), 5.24 (2H, s), 6.78 (1H, d, J=2.8 Hz), 7.05 (1H, dd, J=9.2, 2.8 Hz), 7.16 (1H, d, J=9.2 Hz), 7.25-7.28 (2H, m), 7.43 (1H, s).

ESIMS (+): 658 [M+H]$^+$.

REFERENCE EXAMPLE 31

(S)-2-t-butoxycarbonylamino-4-[2-chloro-4-(5-cyano-2-methoxymethyloxyphenylthio)phenyl]-2-propylbutan-1-ol

[Chemical formula 75]

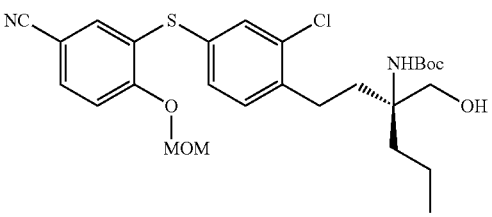

The target product (313 mg) was obtained as a colorless solid by reacting the compound of Reference Example 30 (543 mg) in the same manner as in Reference Example 26.

$^1$H NMR (CDCl$_3$, 400 MHz): δ 0.98 (3H, t, J=7.3 Hz), 1.31-1.45 (2H, m), 1.45 (9H, s), 1.56-1.62 (2H, m), 1.83-1.90 (1H, m), 1.94-2.02 (1H, m), 2.68-2.81 (2H, m), 3.46 (3H, s), 3.75-3.77 (2H, m), 4.20 (1H, brs), 4.66 (1H, s), 5.29 (2H, s), 7.15 (1H, d, J=2.4 Hz), 7.17 (1H, d, J=8.6 Hz), 7.25-7.28 (2H, m), 7.43 (1H, d, J=1.5 Hz), 7.46 (1H, dd, J=8.6, 1.5 Hz).

ESIMS (+): 535 [M+H]$^+$.

REFERENCE EXAMPLE 32

(S)-4-[4-(5-acetyl-2-methoxymethyloxyphenylthio)-2-chlorophenyl]-2-t-butoxycarbonylamino-2-propylbutan-1-ol

[Chemical formula 76]

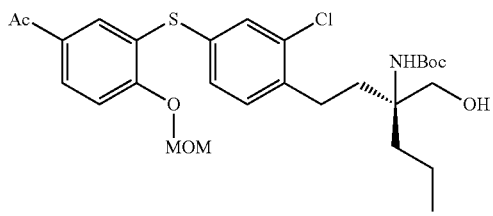

Under an argon gas atmosphere, the compound of Reference Example 30 (525 mg) was dissolved in N,N-dimethylformamide (8.0 mL), and then n-butylvinyl ether (0.512 mL, 3.99 mmol), triethylamine (0.112 mL), palladium acetate (17.9 mg), and 1,3-bis(diphenylphosphino)propane (65.8 mg) were added to form a reaction solution. The reaction solution was then stirred for 5.5 hours at 80° C. 1 mol/L hydrochloric acid was added to the reaction solution under ice cooling, and the reaction solution was then stirred for 1 hour at normal temperature. Water was added to the reaction solution, and the reaction solution was extracted with ethyl acetate. The organic layer was washed 3 times with saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=3:1→1:1) to obtain the target product (373 mg) as a colorless solid.

$^1$H NMR (CDCl$_3$, 400 MHz): δ 0.96 (3H, t, J=7.3 Hz), 1.30-1.44 (2H, m), 1.44 (9H, s), 1.55-1.59 (2H, m), 1.77-1.85 (1H, m), 1.89-1.96 (1H, m), 2.50 (3H, s), 2.62-2.75 (2H, m), 3.38 (3H, s), 3.72-3.74 (2H, m), 4.21 (1H, brs), 4.65 (1H, s), 5.27 (2H, s), 7.14-7.20 (3H, m), 7.30 (1H, d, J=1.8 Hz), 7.83 (1H, d, J=2.1 Hz), 7.87 (1H, dd, J=8.6, 2.1 Hz).
ESIMS (+): 552 [M+H]$^+$.

REFERENCE EXAMPLE 33

(S)-2-t-butoxycarbonylamino-4-[2-chloro-4-(5-cyano-2-methoxymethyloxyphenylthio)phenyl]-1-dimethoxyphosphoryloxy-2-propylbutane

[Chemical formula 77]

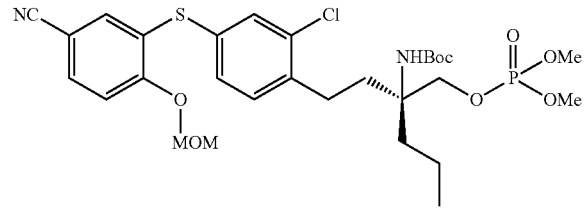

The target product (356 mg) was obtained as a colorless solid by reacting the compound of Reference Example 31 (311 mg) in the same manner as in Reference Example 15.

$^1$H NMR (CDCl$_3$, 400 MHz): δ 0.97 (3H, t, J=7.3 Hz), 1.34-1.45 (2H, m), 1.45 (9H, s), 1.63-1.76 (2H, m), 1.80-1.87 (1H, m), 2.02-2.10 (1H, m), 2.70-2.78 (2H, m), 3.45 (3H, s), 3.79 (3H, d, J=11.0 Hz), 3.80 (3H, d, J=11.0 Hz), 4.13 (1H, dd, J=9.8, 4.3 Hz), 4.27 (1H, dd, J=9.8, 4.3 Hz), 4.54 (1H, brs), 5.29 (2H, s), 7.14 (1H, d, J=1.8 Hz), 7.17 (1H, d, J=8.6 Hz), 7.25-7.27 (2H, m), 7.42 (1H, d, J=1.8 Hz), 7.46 (1H, dd, J=8.6, 1.8 Hz).
ESIMS (+): 643 [M+H]$^+$.

REFERENCE EXAMPLE 34

(S)-4-[4-(5-acetyl-2-methoxymethyloxyphenylthio)-2-chlorophenyl]-2-t-butoxycarbonylamino-1-dimethoxyphosphoryloxy-2-propylbutane

[Chemical formula 78]

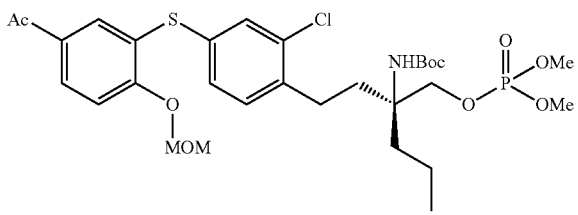

The target product (401 mg) was obtained as a colorless solid by reacting the compound of Reference Example 32 (371 mg) in the same manner as in Reference Example 15.

$^1$H NMR (CDCl$_3$, 400 MHz): δ 0.96 (3H, t, J=7.3 Hz), 1.31-1.42 (2H, m), 1.44 (9H, s), 1.59-1.71 (2H, m), 1.74-1.82 (1H, m), 1.97-2.07 (1H, m), 2.50 (3H, s), 2.64-2.72 (2H, m), 3.38 (3H, s), 3.78 (3H, d, J=11.0 Hz), 3.79 (3H, d, J=11.0 Hz), 4.11 (1H, dd, J=9.8, 4.9 Hz), 4.25 (1H, dd, J=9.8, 4.9 Hz), 4.52 (1H, brs), 5.27 (2H, s), 7.15-7.16 (2H, m), 7.19 (1H, d, J=8.6 Hz), 7.30 (1H, d, J=1.8 Hz), 7.84 (1H, d, J=2.1 Hz), 7.88 (1H, dd, J=8.6, 2.1 Hz).
ESIMS (+): 660 [M+H]$^+$.

REFERENCE EXAMPLE 35

(S)-2-amino-4-[2-chloro-4-(5-cyano-2-hydroxyphenylthio)Phenyl]-2-propylbutylphosphoric acid monoester

[Chemical formula 79]

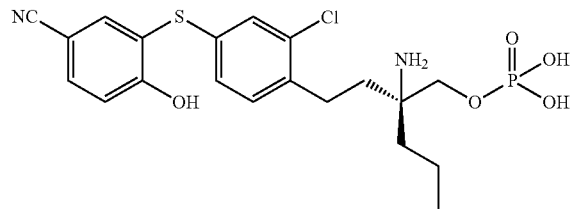

The target product (166 mg) was obtained as a colorless solid by reacting the compound of Reference Example 33 (347 mg) in the same manner as in Example 1.

$^1$H NMR (DMSO-d$_6$, 400 MHz): δ 0.88 (3H, t, J=7.3 Hz), 1.25-1.36 (2H, m), 1.48-1.61 (2H, m), 1.67-1.78 (2H, m), 2.63-2.67 (2H, m), 3.70-3.81 (2H, m), 7.07 (1H, d, J=8.6 Hz), 7.14 (1H, dd, J=8.6, 1.8 Hz), 7.26 (1H, d, J=1.8 Hz), 7.32 (1H, d, J=8.6 Hz), 7.48 (1H, d, J=2.1 Hz), 7.61 (1H, dd, J=8.6, 2.1 Hz).

HRESIMS (+): 471.09108 (Calcd. for $C_{20}H_{25}ClN_2O_5PS$ 471.09103).

REFERENCE EXAMPLE 36

(S)-4-[4-(5-acetyl-2-hydroxyphenylthio)-2-chlorophenyl]-2-amino-2-propylbutylphosphoric acid monoester

[Chemical formula 80]

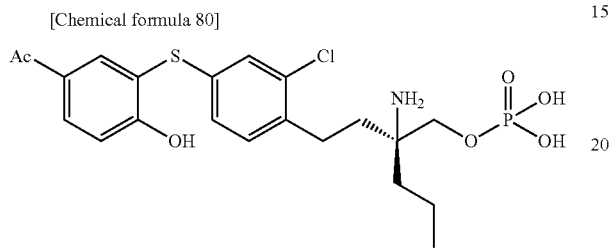

The target product (210 mg) was obtained as a pale yellow solid by reacting the compound of Reference Example 34 (393 mg) in the same manner as in Example 1.

$^1$H NMR (DMSO-$d_6$, 400 MHz): δ 0.88 (3H, t, J=7.3 Hz), 1.24-1.37 (2H, m), 1.51-1.62 (2H, m), 1.68-1.77 (2H, m), 2.44 (3H, s), 2.62-2.66 (2H, m), 3.76-3.85 (2H, m), 7.04 (1H, d, J=8.6 Hz), 7.10 (1H, dd, J=8.6, 1.8 Hz), 7.16 (1H, d, J=1.8 Hz), 7.29 (1H, d, J=8.6 Hz), 7.79 (1H, d, J=2.1 Hz), 7.85 (1H, dd, J=8.6, 2.1 Hz).

HRESIMS (+): 488.10680 (Calcd. for $C_{21}H_{28}ClNO_6PS$ 488.10635).

REFERENCE EXAMPLE 37

(S)-2-t-butoxycarbonylamino-4-{2-chloro-4-(5-ethoxy-2-methoxymethyloxyphenylthio)phenyl}-2-propylbutan-1-ol

[Chemical formula 81]

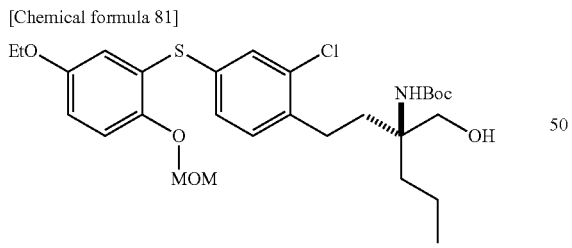

(S)-2-t-butoxycarbonylamino-4-{2-chloro-4-(5-ethoxy-2-hydroxyphenylthio)phenyl}-2-propylbutan-1-ol was obtained by reacting the compound of Reference Example 6 (830 mg) and the compound of Reference Example 10 (403 mg) in the same manner as in Reference Example 13. Then, by further reacting the obtained compound in the same manner as in Reference Example 23, the target product (139 mg) was obtained as a colorless oil.

$^1$H MMR (CDCl$_3$, 400 MHz): δ 0.96 (3H, t, J=7.3 Hz), 1.35 (3H, t, J=6.7 Hz), 1.38-1.42 (1H, m), 1.44 (9H, s), 1.55-1.60 (1H, m), 1.78-1.85 (1H, m), 1.88-1.98 (1H, m), 3.44 (3H, s), 3.74 (2H, q, J=6.7 Hz), 4.15 (1H, brs), 4.63 (1H, brs), 5.12 (2H, s), 6.69 (1H, d, J=3.1 Hz), 7.77 (1H, dd, J=9.2, 3.1 Hz), 7.07 (1H, d, J=9.2 Hz), 7.16-7.17 (2H, m), 7.31-7.32 (1H, m).

ESIMS (+): 554 [M+H]$^+$.

REFERENCE EXAMPLE 38

(S)-2-t-butoxycarbonylamino-4-{2-chloro-4-(5-ethoxy-2-methoxymethyloxyphenylthio)phenyl}-2-propylbutan-1-al

[Chemical formula 82]

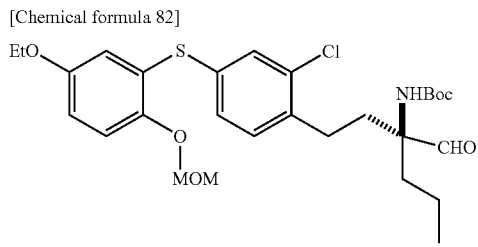

The compound of Reference Example 37 (466 mg) was dissolved in dimethylsulfoxide (4.2 mL), and then triethylamine (1.2 mL) and a sulfur trioxide-pyridine complex (669 mg) were added to form a reaction solution. The reaction solution was then stirred for 1.5 hours at normal temperature. Ice water was added to the reaction solution, and then the reaction solution was extracted with ethyl acetate. The organic layer was successively washed with water and saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=6:1) to obtain the target product (367 mg) as a colorless oil.

$^1$H NMR (CDCl$_3$, 400 MHz): 60.90 (3H, t, J=7.3 Hz), 1.08-1.10 (1H, m), 1.25-1.32 (1H, m), 1.35 (3H, t, J=6.7 Hz), 1.46 (9H, s), 1.59-1.68 (1H, m), 1.96-2.01 (1H, m), 2.12-2.18 (1H, m), 2.43-2.49 (2H, m), 2.57-2.62 (1H, m), 3.44 (3H, s), 3.92 (2H, q, J=6.7 Hz), 5.12 (2H, s), 5.38 (1H, brs), 6.70 (1H, d, J=3.1 Hz), 6.76 (1H, dd, J=9.2, 3.1 Hz), 7.06-7.10 (2H, m), 7.14 (1H, dd, J=8.0, 1.8 Hz), 7.30 (1H, d, J=3.1 Hz), 9.31 (1H, s).

ESIMS (+): 552 [M+H]$^+$.

REFERENCE EXAMPLE 39

Dimethyl (S)-3-t-butoxycarbonylamino-5-{2-chloro-4-(5-ethoxy-2-methoxymethyloxyphenylthio)phenyl}-3-propyl-1-pentenylphosphate

[Chemical formula 83]

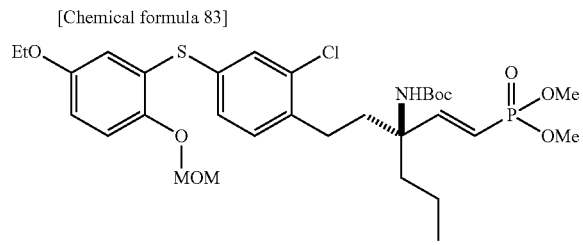

Under an argon gas atmosphere, tetramethyl methylenediphosphonate (201 mg) was dissolved in tetrahydrofuran (7 mL), and then n-butyllithium (1.65 mol/L hexane solution, 0.52 mL) was added dropwise at −78° C. to form a reaction solution. This reaction solution was stirred for 30 minutes at the same temperature. Then, a solution of the compound of Reference Example 38 (367 mg) in tetrahydrofuran (3 mL) was added dropwise to the reaction solution at −78° C., and the reaction solution was stirred for 2 hours at normal temperature. A saturated ammonium chloride aqueous solution was added to the reaction solution, and the reaction solution was extracted with ethyl acetate. The organic layer was washed with saturated brine, and then dried over anhydrous sodium sulfate. The anhydrous sodium sulfate was removed by filtration, and then the solvent was removed by distillation under reduced pressure. The resultant residue was purified by silica gel column chromatography (hexane:ethyl acetate=3:1→1:2) to obtain the target product (369 mg) as a colorless oil.

$^1$H NMR (CDCl$_3$, 400 MHz): δ 0.93 (3H, t, J=7.3 Hz), 1.30-1.32 (4H, m), 1.35 (3H, t, J=6.7 Hz), 1.44 (9H, s), 1.67-1.77 (1H, m), 2.01-2.09 (1H, m), 2.56-2.68 (2H, m), 3.46 (3H, m), 3.72 (3H, s), 3.75 (3H, s), 3.92 (2H, q, J=7.3 Hz), 5.12 (2H, s), 5.67 (1H, t, J=17.7 Hz), 6.69-6.77 (3H, m), 7.07 (1H, d, J=7.3 Hz), 7.11 (1H, d, J=8.0 Hz), 7.15 (1H, dd, J=8.0, 1.8 Hz), 7.31 (1H, d, J=1.8 Hz).

ESIMS (+): 658 [M+H]$^+$.

REFERENCE EXAMPLE 40

Dimethyl (S)-3-t-butoxycarbonylamino-5-(2-chloro-4-(5-ethoxy-2-methoxymethyloxyphenylthio)phenyl)-3-propylpentylphosphonate

[Chemical formula 84]

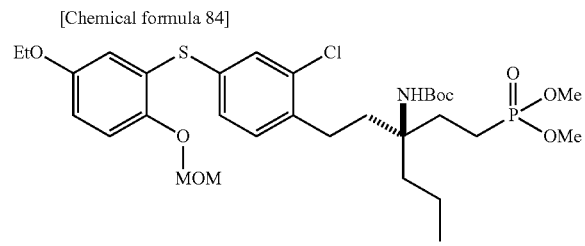

The compound of Reference Example 39 (369 mg) was dissolved in pyridine (11 mL), and then dipotassium azodicarboxylate (1.09 g) and acetic acid (0.48 mL) were added to form a reaction solution. This reaction solution was stirred for 64 hours at normal temperature. The reaction solution was diluted with toluene. Insoluble matter was removed using Celite. The solvent in the filtrate was removed by distillation under reduced pressure. The resultant residue was purified by silica gel column chromatography (hexane:ethyl acetate=1:2) to obtain the target product (150 mg) as a colorless oil.

$^1$H NMR (CDCl$_3$, 400 MHz): δ 0.95 (3H, t, J=7.3 Hz), 1.24-1.56 (4H, m), 1.35 (3H, t, J=7.3 Hz), 1.43 (9H, s), 1.69-1.77 (2H, m), 1.85-2.10 (3H, m), 2.60-2.64 (2H, m), 3.44 (3H, m), 3.73 (3H, s), 3.76 (3H, s), 3.92 (2H, q, J=7.3 Hz), 4.27 (1H, brs), 5.12 (2H, s), 6.69 (1H, d, J=3.1 Hz), 6.76 (1H, dd, J=9.2, 3.1 Hz), 7.07 (1H, d, J=9.2 Hz), 7.12 (1H, d, J=8.0 Hz), 7.16 (1H, dd, J=8.0, 1.8 Hz), 7.31 (1H, d, J=1.8 Hz).

ESIMS (+): 660 [M+H]$^+$.

EXAMPLE 3

(S)-3-amino-5-{2-chloro-4-(5-ethoxy-2-hydroxyphenylthio)phenyl}-3-propylpentylphosphonic acid

[Chemical formula 85]

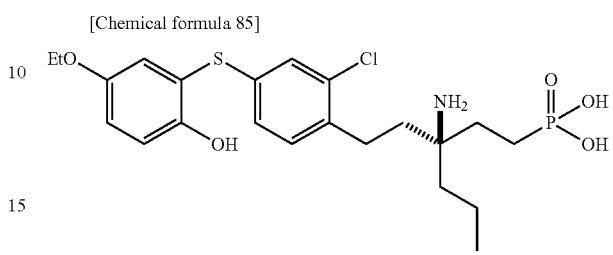

The target product (60 mg) was obtained as a colorless solid by reacting the compound of Reference Example 40 (145 mg) in the same manner as Example 1.

Optical rotation: [α]$_D^{23}$ +1.8 (c 0.32, MeOH).

$^1$H NMR (DMSO-d$_5$, 400 MHz): δ 0.88 (3H, t, J=7.3 Hz), 1.23 (3H, t, J=6.7 Hz), 1.29 (2H, brs), 1.54 (4H, brs), 1.70-1.81 (4H, m), 2.61 (2H, brs), 3.87 (2H, q, J=6.7 Hz), 6.70 (1H, d, J=3.1 Hz), 6.80-6.88 (2H, m), 7.09-7.12 (2H, m), 7.28 (1H, d, J=8.0 Hz).

HRESIMS (+): 488.14296 (Calcd. for C$_{22}$H$_{32}$ClNO$_5$PS 488.14273).

Results supporting the effectiveness of the compounds illustrated as examples will now be shown in Experiment Examples 1, 2, and 3.

EXPERIMENT EXAMPLE 1

Suppression Effect of Test Compound Against Cellular Calcium Mobilization of Human S1P3 Receptor-Expression Cell by S1P (Sphingosine 1-Phosphoric Acid)

Human S1P3 receptor-expression CHO cells were subcultured in a Ham's F-12 culture medium containing 10% fetal bovine serum, and 300 μg/mL of Geneticin The human S1P3 receptor-expression CHO cells were subjected to 0.25% trypsinization, then recovered from the dish, and floated in a Ham's F-12 culture medium containing 10% fetal bovine serum, and 300 μg/mL of Geneticin. Then, the human S1P3 receptor-expression CHO cells were seeded into a 96-well black clear bottom plate (BD Falcon Biocoat) at 2.5×10$^4$/100 μL/well. The human S1P3 receptor-expression CHO cells were then cultivated for two nights at 37° C. under 5% CO$_2$ environment. The next day, the wells were washed with a Ham's F-12 culture medium containing 100 μL of 0.1% fatty acid-free bovine serum albumin (BSA). This washing treatment was carried out 3 times. The culture medium was exchanged with a Ham's F-12 culture medium containing 0.1% BSA, and then starved of serum for 6 hours in a CO$_2$ incubator set at 37° C.

The culture medium was thrown away after the 6 hours. Then, 50 μL/well of a Fluo3 loading buffer was added, and the cultures were cultivated for further 1 hour. The Fluo3 loading buffer was prepared as follows. First, equal amounts of Fluo3-AM (Dojindo) and pluronic F-127 (20% DMSO solution, invitrogen) were mixed. Then, the mixture of Fluo3-AM and pluronic F-127 was added into a Hanks-HEPES buffer (Hanks balanced salt solution containing 20 mM HEPES (pH 7.4), 0.1% BSA (fatty acid-free), and 2.5 mM probenecid) to form a Fluo3 loading buffer having a final Fluo3-AM concentration of 4 µM.

After incubating for 1 hour, the wells were washed 3 times with 100 µL of the Hanks-HEPES buffer. 100 µL of the same buffer in which a test compound (0.125 nM, 1.25 nM, 12.5 nM, 125 nM, 1.25 µM) or DMSO had been dissolved were added to the each well, and then incubated for 30 minutes at 37° C. in a microplate spectrophotofluorometer (FLEX Station (Molecular Device Co., Ltd.)). Then, 25 µL of S1P prepared at 5 times the concentration of the final concentration based on serial dilution (final concentration of 0.1 nM, 1 nM, 10 nM, 100 nM, and 1 µM) was added, and the fluorescence based on the Fluo3 due to calcium mobilization was detected and measured at an excitation wavelength of 485 nm and a detection wavelength of 525 nm using an same apparatus. Based on the measurement data, the increase in fluorescence was calculated by subtracting the minimum fluorescence intensity from the maximum fluorescence intensity. The calculated increase in fluorescence was used to perform a curve approximation of the relationship between the S1P concentration and the increase in fluorescence using PRISM 4 software (GraphPad). Based on the results, the EC50 value of the compound-untreated and the EC50 value of the compound-treated at each concentration was calculated. Based on these values, Schild plot analysis was carried out in order to determine the dissociation constant Kd. The results are shown in Table 1. In Table 1, 1 nmol/L>Kd value≥0.1 nmol/L is indicated as "+", 0.1 nmol/L>Kd value≥0.01 nmol/L is indicated as "++", and 0.01 nmol/L>Kd value is indicated as "+++".

TABLE 1

|  | S1P3 |
| --- | --- |
| Example 1 | +++ |
| Example 2 | +++ |
| Reference Example 19 | + |
| Reference Example 28 | + |
| Reference Example 35 | + |
| Reference Example 36 | + |

EXPERIMENT EXAMPLE 2

Intracellular Calcium Mobilization Derivative Test of Test Compound Against Human S1P1 Receptor-Expression Cell Human S1P1 receptor-expression CHO cells were subcultured in a Ham's F-12 culture medium containing 10% fetal bovine serum, and 300 µg/mL of Geneticin. The human S1P1 receptor-expression CHO cells were subjected to 0.25% trypsinization, then recovered from the dish, and floated in a Ham's F-12 culture medium containing 10% fetal bovine serum, and 300 µg/mL of Geneticin. Then, the human S1P1 receptor-expression CHO cells were seeded into a 96-well black clear bottom plate (BD Falcon Biocoat) at $2.5 \times 10^4$/100 µL/well. The human S1P3 receptor-expression CHO cells were then cultivated for two nights at 37° C. under 5% $CO_2$ environment. The next day, the wells were washed with a Ham's F-12 culture medium containing 100 µL of 0.1% fatty acid-free bovine serum albumin (BSA). This washing treatment was carried out 3 times. The culture medium was exchanged with a Ham's F-12 culture medium containing 0.1% BSA, and then starved of serum for 6 hours in a $CO_2$ incubator set at 37° C.

The culture medium was thrown away after the 6 hours. Then, 50 µL/well of a Fluo3 loading buffer was added, and the cultures were cultivated for further 1 hour. The Fluo3 loading buffer was prepared as follows. First, equal amounts of Fluo3-AM (Dojindo) and pluronic F-127(20% DMSO solution, invitrogen) were mixed. Then, the mixture of Fluo3-AM and pluronic F-127 was added into a Hanks-HEPES buffer (Hanks balanced salt solution containing 20 mM HEPES (pH 7.4), 0.1% BSA (fatty acid-free), and 2.5 mM probenecid) to form a Fluo3 loading buffer having a final Fluo3-AM concentration of 4 µM.

After incubating for 1 hour, the wells were washed 3 times with 100 µL of the Hanks-HEPES buffer. Next, 100 µL of the same buffer was added, and then the cultures were incubated for 15 minutes at 37° C. in a microplate spectrophotofluorometer (FLEX Station (Molecular Device Co., Ltd.)). Then, 25 µL of the same buffer dissolved with DMSO, or S1P prepared at 5 times the concentration of the final concentration based on serial dilution or the test compound (final concentration of 0.1 nM, 1 nM, 10 nM, 100 nM, 1 µM, and 10 µM) was added, and the fluorescence based on the Fluo3 due to calcium mobilization was detected and measured at an excitation wavelength of 485 nm and a detection wavelength of 525 nm using the same apparatus. Based on the measurement data, the increase in fluorescence was calculated by subtracting the minimum fluorescence intensity from the maximum fluorescence intensity. The percentage increase in fluorescence (%) of the test compound was calculated based on a difference of 100% between the increase in fluorescence when the solvent was added and the increase in fluorescence when acted on by $10^{-6}$ M S1P. The $EC_{50}$ value was determined using PRISM software (GraphPad) as the intracellular calcium mobilization derivative action of the test compound.

The $EC_{50}$ value of the compounds of Example 1 and Example 2 was greater than 10 µmol/L (>10 µmol/L). Further, an evaluation of the antagonistic action of the S1P1 receptor using the method of Experiment Example 1 showed that the Kd value of the compounds of Example 1 and Example 2 was 2.66 nmol/L and 1.60 nmol/L, respectively.

EXPERIMENTAL EXAMPLE 3

Cecal Ligation and Puncture Sepsis Model

This model is widely used as a model for polymicrobial abdominal sepsis caused by leakage of intestinal bacteria. The experiment was carried out with reference to the method described in Non-Patent Literature 9 (D. Rittirsch et al., Nature Protocols, 4, 31 (2009)).

Preparation of Cecalligation and Puncture (CLP) Sepsis Mice

Wistar rats (Charles River Laboratories, Japan Inc., male 8 W) were used. The abdominal portion of the rats was cut open under isoflurane anesthesia, and the appendix was exteriorized. The appendix was ligated with sterilized silk thread, and 10 holes were opened in the tip portion of the appendix using an 18 G syringe needle. After the treatment, the appendix was returned to the body, and the wound was sutured. Further, physiological saline was subcutaneously administered at a dose of 30 mL/kg. The rats were then returned to their cages, and observed for 7 days to determine the survival rate.

Test Compound Administration Method

The test compound was continuously administered via a cannula stuck in the femoral vein at a dose of 0.1 mg/kg/hr.

Administration of the test compound was started 1 hour after the CLP procedure was finished.

For the group administered with the compound of Example 2, a statistically significant effect was found (survival lengthening action, Log-rank test p<0.01) that shifted the survival curve to the right as compared with the medium administration group. Further, although all of the test subjects died within 1 day for the medium administration group, for the group administered with the compound of Example 2, a survival rate improvement action was found, with 25% of the test subjects alive after 3 days, while 12.5% were alive even after 7 days. These results suggest that the compound of Example 2 is effective against sepsis.

Based on the above results, it is clear that despite exhibiting an excellent antagonistic action against the human S1P3 receptor, the compound of the present invention exhibits a weaker or no antagonistic action or agonistic action against the S1P1 receptor as compared with human S1P3 receptor antagonistic action. Further, it was also confirmed that the compound of the present invention exhibits an excellent suppressive effect against sepsis.

Industrial Applicability

According to the present invention, a diphenyl sulfide derivative having an excellent S1P3 antagonistic activity and S1P3 selectivity can be provided. Further, the diphenyl sulfide derivative of the present invention can be stably used as a medicine as it causes little or no hemolysis, tissue damage, or central depressant action. In addition, the diphenyl sulfide derivative of the present invention is stable in aqueous solution. The compound of the present invention having these excellent properties is effective as a preventive or a therapeutic medicine for respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, sepsis, cytokine storm caused by an influenza virus or RS virus infection, arteriosclerosis, blood vessel intimal thickening, solid tumors, diabetic retinopathy, articular rheumatism, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema such as ARDS, cardiac arrhythmia, eye disease, eye hypertension, glaucoma, glaucomatous retinopathy, optic neuropathy, and macula-lutea degeneration.

The invention claimed is:

1. A diphenyl sulfide derivative, or a pharmaceutically acceptable salt or hydrate thereof, represented by
    an (S)-2-amino-4-{2-chloro-4-(5-ethoxy-2-hydroxyphenylthio)phenyl}-2-propylbutylphosphoric acid monoester.

2. A medicine, comprising the diphenyl sulfide derivative according to claim 1, or a pharmaceutically acceptable salt or hydrate thereof.

3. The medicine according to claim 2, wherein the medicine is a therapeutic or preventive medicine for respiratory tract contraction, bronchial asthma, chronic obstructive pulmonary disease (COPD), pulmonary emphysema, tracheal stenosis, diffuse panbronchiolitis, bronchitis resulting from infection, connective tissue disease, or transplantation, diffuse pulmonary hamartoangiomyomatosis, adult respiratory distress syndrome (ARDS), interstitial pneumonitis, lung cancer, pneumonia hypersensitivity, idiopathic interstitial pneumonia, fibrosis of the lung, sepsis, or cytokine storm caused by an influenza virus or RS virus infection.

4. The medicine according to claim 2, wherein the medicine is a therapeutic or preventive medicine for arteriosclerosis, blood vessel intimal thickening, solid tumors, diabetic retinopathy, rheumatoid arthritis, cardiac arrest, ischemia-reperfusion disorders, cerebral blood vessel spasms after subarachnoid bleeding, angina pectoris or myocardial infarction caused by coronary vessel spasms, glomerulonephritis, thrombosis, lung disease caused by pulmonary edema, cardiac arrhythmia, eye disease, eye hypertension, glaucoma, glaucomatous retinopathy, optic neuropathy, or macula-lutea degeneration.

5. The medicine according to claim 2, wherein the medicine is a therapeutic or preventive medicine for sepsis.

6. A pharmaceutical composition, comprising the diphenyl sulfide derivative according to claim 1, or a pharmaceutically acceptable salt or hydrate thereof, and a pharmaceutically acceptable carrier.

* * * * *